(12) United States Patent
Ippikoglou

(10) Patent No.: US 7,560,528 B2
(45) Date of Patent: Jul. 14, 2009

(54) METHOD OF PRODUCING RECOMBINANT DNA MOLECULES

(76) Inventor: Efthimios Ippikoglou, 7 Ntolgopolof, Drosia, Athens (GR)

( * ) Notice: Subject to any disclaimer, the term of this patent is extended or adjusted under 35 U.S.C. 154(b) by 0 days.

(21) Appl. No.: 10/561,743

(22) PCT Filed: Jun. 18, 2004

(86) PCT No.: PCT/EP2004/006600

§ 371 (c)(1), (2), (4) Date: Dec. 20, 2005

(87) PCT Pub. No.: WO2004/113565

PCT Pub. Date: Dec. 29, 2004

(65) Prior Publication Data

US 2006/0177826 A1    Aug. 10, 2006

Related U.S. Application Data

(60) Provisional application No. 60/493,586, filed on Aug. 7, 2003, provisional application No. 60/480,581, filed on Jun. 20, 2003.

(51) Int. Cl.
*A61K 38/17* (2006.01)
*C12N 5/10* (2006.01)
*A61K 39/00* (2006.01)
*C07H 17/00* (2006.01)

(52) U.S. Cl. .................. 530/350; 424/192.1; 536/23.1

(58) Field of Classification Search .................. None
See application file for complete search history.

(56) References Cited

U.S. PATENT DOCUMENTS

| 5,023,171 | A | 6/1991 | Ho et al. |
| 5,512,661 | A | 4/1996 | Shooter et al. |
| 5,891,855 | A * | 4/1999 | Florkiewicz ................. 514/26 |
| 6,183,987 | B1 | 2/2001 | van de Wiel et al. |
| 6,238,890 | B1 * | 5/2001 | Boime et al. ............... 435/69.7 |
| 7,081,446 | B2 * | 7/2006 | Lustbader ..................... 514/13 |

FOREIGN PATENT DOCUMENTS

| WO | WO-99/16904 A1 | 4/1999 |
| WO | WO-99/58721 A | 11/1999 |

* cited by examiner

*Primary Examiner*—Michael Pak
*Assistant Examiner*—Nirmal S Basi
(74) *Attorney, Agent, or Firm*—Konstantina M. Katcheves; Saul Ewing LLP

(57) ABSTRACT

The present invention is directed to an improved method for producing by recombinant methods proteins that occur in nature in two or more subunits; more specifically applicable to proteins that comprise the alpha and beta subunit of FSH.

2 Claims, 4 Drawing Sheets

```
                        SEQUENCE LISTING

<160> NUMBER OF SEQ ID NOS: 31

<210> SEQ ID NO 1
<211> LENGTH: 1909
<212> TYPE: DNA
<213> ORGANISM: Homo sapiens
<220> FEATURE:
<221> NAME/KEY: misc_feature
<222> LOCATION: (1)..(1909)
<223> OTHER INFORMATION: cDNA sequence for human b-FSH

<400> SEQUENCE: 1
acagctcttg ccaggcaagg cagccgacca cagaccagga tgaagacact ccagttttc        60 ttccttttct gttgctggaa agcaatctgc tgcaatagct gtgagctgac caacatcacc     120
attgcaatag agaaagaaga atgtcgtttc tgcataagca tcaacaccac ttggtgtgct     180
ggctactgct acaccaggga tctggtgtat aaggacccag ccaggcccaa aatccagaaa     240
acatgtacct tcaaggaact ggtatatgaa acagtgagag tgcccggctg tgctcaccat     300
gcagattcct tgtatacata cccagtgcc acccagtgtc actgtggcaa gtgtgacagc      360
gacagcactg attgtactgt gcgaggcctg gggcccagct actgctcctt tggtgaaatg     420
aaagaataaa gatcagtgga catttcaggc cacataccct tgtcctgaag gaccaagata     480
ttcaaaaagt ctgtgtgtgt gcaatgtgcc caggggacaa accactggat cagggggattc    540 agactctact gatccctggt ctactggcag agggaactct gggaattgag agtgctgggg     600
gccaggactc catcatgatt cagctctata ttcctaggtc tgatttcata aggtttattc     660
agtcttaact cacagacttg tgcctggttt cttcttaaa aatcttagaa atcttctcag      720
gcaatgcctc tctcttaggg ggaaacataa gcctagaagg aggaagcagt aatgggagtg     780
agtgaaagaa ctaactgcag cagtcttctg gtagactctt gggccctcta gagcaaggtc     840
agcatcttca gcattgtagc gtcaatgcct agcactctgc ctggaactta gaaacacaac     900
aatggcttct ttagatcaga aaggtcaagg gtagaaaata ctggaagagg atgtttgagg     960
taagctgatg aggctgcccg cagcacacca gtcccatgaa agttagtggc atcagtttca    1020
cctcgccttt tctccagcac atgagtattg agacatgatg tgtctttctg aattgtttgg    1080
tacagatggg gagtaacaga gctcgaagat ttccaagcta ttactaccaa gcctgttagt    1140
taagggcaaa ggcaagaaat tgtaatttgg ggctgtggaa attagcctgc ctctattcat    1200
tacttaaaca aattgatcac atgctactag gctcctgcaa actccttttt gagataaagg    1260
gaaaaaacca aactatctca ccctaccctc cctaggatcc acttctttgg aatgacaaag    1320
gatttgaaag taggtttgaa agcagtttca gcaatttaat aaatataatt aatttgtcta    1380
ccaaatatat ttgtataaat aatagctcct ttagaaagaa ttagccatgg ggggatcgag    1440
gggaaactgc tgtttctag gatcctgtct acatcaatct tctatttat ccatccatgt      1500 tctcccaaat ctgtgctttc tttcaacagg ttatatatta aaactatttc atgagttgat    1560 ttctttttaaa cgtgttaact gtcttagtta tgcactcagt ttcacactca tattgtttaa   1620
ctaatttatt taaagtctta tttttttaat aaagatgcta gccaccagag tcacggcttg    1680
gattgtttta tgtacaaaca gatgacttag aaattctgta ttttataata atattagtgg    1740
```

-continued

```
aatgaaatct taaaatataa ttcccagtgt ttctataaat attacctttc cttatctttg    1800
gagatattaa aaataatttt gttggatttc tgaagtgttt tgtcacttaa atttcctgtc    1860
attttttgaa gacattttct gatgtaattt gggagaaaaa aagcataga               1909

<210> SEQ ID NO 2
<211> LENGTH: 54
<212> TYPE: DNA
<213> ORGANISM: Homo sapiens
<220> FEATURE:
<221> NAME/KEY: misc_feature
<222> LOCATION: (1)..(5)
<223> OTHER INFORMATION: B-FSH signal sequence

<400> SEQUENCE: 2
atgaagacac tccagttttt cttccttttc tgttgctgga aagcaatctg ctgc          54

<210> SEQ ID NO 3
<211> LENGTH: 159
<212> TYPE: DNA
<213> ORGANISM: Homo sapiens
<220> FEATURE:
<221> NAME/KEY: exon
<222> LOCATION: (1)..(159)
<223> OTHER INFORMATION: exon #1 of human B-FSH (NM_000510)

<400> SEQUENCE: 3 atg aag aca ctc cag ttt ttc ttc ctt ttc tgt tgc tgg aaa gca atc     48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa     96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc     144
Glu Glu Cys Arg Phe Cys Ile Ser Ile Asn Thr Thr Trp Cys Ala Gly
        35                  40                  45 tac tgc tac acc agg                                                  159
Tyr Cys Tyr Thr Arg
    50

<210> SEQ ID NO 4
<211> LENGTH: 231
<212> TYPE: DNA
<213> ORGANISM: Homo sapiens
<220> FEATURE:
<221> NAME/KEY: exon
<222> LOCATION: (1)..(231)
<223> OTHER INFORMATION: exon #2 of human B-FSH (NM_000510)

<400> SEQUENCE: 4 gat ctg gtg tat aag gac cca gcc agg ccc aaa atc cag aaa aca tgt     48
Asp Leu Val Tyr Lys Asp Pro Ala Arg Pro Lys Ile Gln Lys Thr Cys
1               5                   10                  15 acc ttc aag gaa ctg gta tat gaa aca gtg aga gtg ccc ggc tgt gct     96
Thr Phe Lys Glu Leu Val Tyr Glu Thr Val Arg Val Pro Gly Cys Ala
            20                  25                  30 cac cat gca gat tcc ttg tat aca tac cca gtg gcc acc cag tgt cac     144
His His Ala Asp Ser Leu Tyr Thr Tyr Pro Val Ala Thr Gln Cys His
        35                  40                  45 tgt ggc aag tgt gac agc gac agc act gat tgt act gtg cga ggc ctg     192
Cys Gly Lys Cys Asp Ser Asp Ser Thr Asp Cys Thr Val Arg Gly Leu
    50                  55                  60 ggg ccc agc tac tgc tcc ttt ggt gaa atg aaa gaa taa                  231
Gly Pro Ser Tyr Cys Ser Phe Gly Glu Met Lys Glu
```

<210> SEQ ID NO 5
<211> LENGTH: 129
<212> TYPE: PRT
<213> ORGANISM: Homo sapiens

<400> SEQUENCE: 5

```
Met Lys Thr Leu Gln Phe Phe Phe Leu Phe Cys Cys Trp Lys Ala Ile
 1               5                  10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu
```

<210> SEQ ID NO 6
<211> LENGTH: 390
<212> TYPE: DNA
<213> ORGANISM: Artificial Sequence
<220> FEATURE:
<223> OTHER INFORMATION: B-FSH X1X2 PCR product
<300> PUBLICATION INFORMATION:
<308> DATABASE ACCESSION NUMBER: GenBank / NM_000510
<309> DATABASE ENTRY DATE: 2002-11-05
<313> RELEVANT RESIDUES: (1)..(390)

<400> SEQUENCE: 6

```
atgaagacac tccagttttt cttccttttc tgttgctgga aagcaatctg ctgcaatagc      60
tgtgagctga ccaacatcac cattgcaata gagaaagaag aatgtcgttt ctgcataagc     120
atcaacacca cttggtgtgc tggctactgc tacaccaggg atctggtgta taaggaccca     180
gccaggccca aaatccagaa aacatgtacc ttcaaggaac tggtatatga aacagtgaga     240
gtgcccggct gtgctcacca tgcagattcc ttgtatacat cccagtggc cacccagtgt     300 cactgtggca agtgtgacag cgacagcact gattgtactg tgcgaggcct ggggcccagc     360
tactgctcct tggtgaaat gaaagaataa                                       390
```

<210> SEQ ID NO 7
<211> LENGTH: 25
<212> TYPE: DNA
<213> ORGANISM: Artificial Sequence
<220> FEATURE:
<223> OTHER INFORMATION: primer PFX1 n.t. position 40-64 in SEQ ID NO:
      1, cDNA sequence for human B-FSH

<400> SEQUENCE: 7

```
atgaagacac tccagttttt cttcc                                            25
```

<210> SEQ ID NO 8

```
<211> LENGTH: 21
<212> TYPE: DNA
<213> ORGANISM: Artificial Sequence
<220> FEATURE:
<223> OTHER INFORMATION: primer PRX1 n.t. position 198-178 in SEQ ID NO:
      1, cDNA sequence for human B-FSH

<400> SEQUENCE: 8
cctggtgtag cagtagccag c                                              21

<210> SEQ ID NO 9
<211> LENGTH: 21
<212> TYPE: DNA
<213> ORGANISM: Artificial Sequence
<220> FEATURE:
<223> OTHER INFORMATION: primer PFX2 n.t. position 199-219 in SEQ ID NO:
      1, cDNA sequence for human B-FSH

<400> SEQUENCE: 9
gatctggtgt ataaggaccc a                                              21

<210> SEQ ID NO 10
<211> LENGTH: 23
<212> TYPE: DNA
<213> ORGANISM: Artificial Sequence
<220> FEATURE:
<223> OTHER INFORMATION: primer PRX2 n.t. position 429-407 in SEQ ID NO:
      1, cDNA sequence for human B-FSH

<400> SEQUENCE: 10
ttattctttc atttcaccaa agg                                            23

<210> SEQ ID NO 11
<211> LENGTH: 42
<212> TYPE: DNA
<213> ORGANISM: Artificial Sequence
<220> FEATURE:
<223> OTHER INFORMATION: primer PRX1-PFX2'

<400> SEQUENCE: 11
tgggtcctta tacaccagat ccctggtgta gcagtagcca ga                       42

<210> SEQ ID NO 12
<211> LENGTH: 39
<212> TYPE: DNA
<213> ORGANISM: Artificial Sequence
<220> FEATURE:
<223> OTHER INFORMATION: primer SDK-PFX1

<400> SEQUENCE: 12
tcgaaggaga tagaatgaag acactccagt ttttcttcc                           39

<210> SEQ ID NO 13
<211> LENGTH: 180
<212> TYPE: DNA
<213> ORGANISM: Homo sapiens
<220> FEATURE:
<221> NAME/KEY: misc_feature
<222> LOCATION: (1)..(180)
<223> OTHER INFORMATION: X1UR product

<400> SEQUENCE: 13
atgaagacac tccagttttt cttccttttc tgttgctgga aagcaatctg ctgcaatagc    60
tgtgagctga ccaacatcac cattgcaata gagaaagaag aatgtcgttt ctgcataagc   120
atcaacacca cttggtgtgc tggctactgc tacaccaggg atctggtgta taaggaccca   180
```

<210> SEQ ID NO 14
<211> LENGTH: 704
<212> TYPE: DNA
<213> ORGANISM: Homo sapiens
<220> FEATURE:
<221> NAME/KEY: misc_feature
<222> LOCATION: (1)..(704)
<223> OTHER INFORMATION: alpha-FSH (NM_000735) full length cDNA sequence

<400> SEQUENCE: 14

```
gcagttactg agaactcata agacgaagct aaaatccctc ttcggatcca cagtcaaccg      60
ccctgaacac atcctgcaaa agcccagag aaggagcgc catggattac tacagaaaat     120
atgcagctat ctttctggtc acattgtcgg tgtttctgca tgttctccat tccgctcctg     180
atgtgcagga ttgcccagaa tgcacgctac aggaaaaccc attcttctcc cagccgggtg     240
ccccaatact tcagtgcatg ggctgctgct tctctagagc atatcccact ccactaaggt     300
ccaagaagac gatgttggtc caaaagaacg tcacctcaga gtccacttgc tgtgtagcta     360
aatcatataa cagggtcaca gtaatggggg gtttcaaagt ggagaaccac acggcgtgcc     420
actgcagtac ttgttattat cacaaatctt aaatgtttta ccaagtgctg tcttgatgac     480
tgctgatttt ctggaatgga aaattaagtt gtttagtgtt tatggctttg tgagataaaa     540
ctctcctttt ccttaccata ccactttgac acgcttcaag gatatactgc agctttactg     600
ccttcctcct tatcctacag tacaatcagc agtctagttc ttttcatttg gaatgaatac     660
agcattaagc ttgttccact gcaaataaag ccttttaaat catc                      704
```

<210> SEQ ID NO 15
<211> LENGTH: 30
<212> TYPE: DNA
<213> ORGANISM: Artificial Sequence
<220> FEATURE:
<223> OTHER INFORMATION: PCR primer HCG-SENT

<400> SEQUENCE: 15

```
atggattact acagaaaata tgcagctatc                                       30
```

<210> SEQ ID NO 16
<211> LENGTH: 30
<212> TYPE: DNA
<213> ORGANISM: Artificial Sequence
<220> FEATURE:
<223> OTHER INFORMATION: PCR primer HCG-ANTISENT

<400> SEQUENCE: 16

```
ttaagatttg tgataataac aagtactgca                                       30
```

<210> SEQ ID NO 17
<211> LENGTH: 351
<212> TYPE: DNA
<213> ORGANISM: Artificial Sequence
<220> FEATURE:
<223> OTHER INFORMATION: glycalA - RT-PCR product

<400> SEQUENCE: 17

```
atggattact acagaaaata tgcagctatc tttctggtca cattgtcggt gtttctgcat      60
gttctccatt ccgctcctga tgtgcaggat tgcccagaat gcacgctaca ggaaaaccca     120
ttcttctccc agccgggtgc cccaatactt cagtgcatgg gctgctgctt ctctagagca     180
tatcccactc cactaaggtc caagaagacg atgttggtcc aaaagaacgt cacctcagag     240
tccacttgct gtgtagctaa atcatataac agggtcacag taatgggggg tttcaaagtg     300
```
gagaaccaca cggcgtgcca ctgcagtact tgttattatc acaaatctta a        351

<210> SEQ ID NO 18
<211> LENGTH: 34
<212> TYPE: DNA
<213> ORGANISM: Artificial Sequence
<220> FEATURE:
<223> OTHER INFORMATION: PCR primer HCG-SENTCACC

<400> SEQUENCE: 18
caccatggat tactacagaa aatatgcagc tatc        34

<210> SEQ ID NO 19
<211> LENGTH: 355
<212> TYPE: DNA
<213> ORGANISM: Artificial Sequence
<220> FEATURE:
<223> OTHER INFORMATION: PCR product CACCglycalA

<400> SEQUENCE: 19
caccatggat tactacagaa aatatgcagc tatctttctg gtcacattgt cggtgtttct        60
gcatgttctc cattccgctc ctgatgtgca ggattgccca gaatgcacgc tacaggaaaa       120
cccattcttc tcccagccgg gtgccccaat acttcagtgc atgggctgct gcttctctag       180
agcatatccc actccactaa ggtccaagaa gacgatgttg gtccaaaaga acgtcacctc       240
agagtccact tgctgtgtag ctaaatcata taacagggtc acagtaatgg ggggtttcaa       300
agtggagaac cacacggcgt gccactgcag tacttgttat tatcacaaat cttaa           355

<210> SEQ ID NO 20
<211> LENGTH: 684
<212> TYPE: DNA
<213> ORGANISM: Artificial Sequence
<220> FEATURE:
<223> OTHER INFORMATION: PCR product AB-FSH

<400> SEQUENCE: 20
atggattact acagaaaata tgcagctatc tttctggtca cattgtcggt gtttctgcat        60
gttctccatt ccgctcctga tgtgcaggat tgcccagaat gcacgctaca ggaaaaccca       120
ttcttctccc agccgggtgc cccaatactt cagtgcatgg gctgctgctt ctctagagca       180
tatcccactc cactaaggtc caagaagacg atgttggtcc aaaagaacgt cacctcagag       240
tccacttgct gtgtagctaa atcatataac agggtcacag taatgggggg tttcaaagtg       300
gagaaccaca cggcgtgcca ctgcagtact tgttattatc acaaatctaa tagctgtgag       360
ctgaccaaca tcaccattgc aatagagaaa gaagaatgtc gtttctgcat aagcatcaac       420
accacttggt gtgctggcta ctgctacacc agggatctgg tgtataagga cccagccagg       480
cccaaaatcc agaaaacatg taccttcaag gaactggtat atgaaacagt gagagtgccc       540
ggctgtgctc accatgcaga ttccttgtat acatacccag tggccaccca gtgtcactgt       600
ggcaagtgtg acagcgacag cactgattgt actgtgcgag gcctgggggc cagctactgc       660
tccttttggtg aaatgaaaga ataa       684

<210> SEQ ID NO 21
<211> LENGTH: 20
<212> TYPE: DNA
<213> ORGANISM: Artificial Sequence
<220> FEATURE:
<223> OTHER INFORMATION: PCR forward primer PFMX2

<400> SEQUENCE: 21
aatagctgtg agctgaccaa                                                                      20

<210> SEQ ID NO 22
<211> LENGTH: 336
<212> TYPE: DNA
<213> ORGANISM: Artificial Sequence
<220> FEATURE:
<223> OTHER INFORMATION: PCR product S-FSH-B

<400> SEQUENCE: 22
aatagctgtg agctgaccaa catcaccatt gcaatagaga agaagaatg tcgtttctgc          60 ataagcatca acaccacttg gtgtgctggc tactgctaca ccagggatct ggtgtataag        120
gacccagcca ggcccaaaat ccagaaaaca tgtaccttca aggaactggt atatgaaaca        180
gtgagagtgc ccggctgtgc tcaccatgca gattccttgt atacataccc agtggccacc       240
cagtgtcact gtggcaagtg tgacagcgac agcactgatt gtactgtgcg aggcctgggg      300
cccagctact gctcctttgg tgaaatgaaa gaataa                                              336

<210> SEQ ID NO 23
<211> LENGTH: 31
<212> TYPE: DNA
<213> ORGANISM: Artificial Sequence
<220> FEATURE:
<223> OTHER INFORMATION: PCR primer HCG-ANTISENT/woTAA

<400> SEQUENCE: 23
agatttgtga taataacaag tactgcagtg g                                                    31

<210> SEQ ID NO 24
<211> LENGTH: 348
<212> TYPE: DNA
<213> ORGANISM: Artificial Sequence
<220> FEATURE:
<223> OTHER INFORMATION: PCR product glycalwoTAA

<400> SEQUENCE: 24
atggattact acagaaaata tgcagctatc tttctggtca cattgtcggt gtttctgcat          60
gttctccatt ccgctcctga tgtgcaggat tgcccagaat gcacgctaca ggaaaaccca      120
ttcttctccc agccgggtgc cccaatactt cagtgcatgg gctgctgctt ctctagagca       180
tatcccactc cactaaggtc caagaagacg atgttggtcc aaaagaacgt cacctcagag      240
tccacttgct gtgtagctaa atcatataac agggtcacag taatggggggg tttcaaagtg     300 gagaaccaca cggcgtgcca ctgcagtact tgttattatc acaaatct                               348

<210> SEQ ID NO 25
<211> LENGTH: 51
<212> TYPE: DNA
<213> ORGANISM: Artificial Sequence
<220> FEATURE:
<223> OTHER INFORMATION: hybrid reverse primer ABLIGATION

<400> SEQUENCE: 25
ttggtcagct cacagctatt agatttgtga taataacaag tactgcagtg g                  51

<210> SEQ ID NO 26
<211> LENGTH: 368
<212> TYPE: DNA
<213> ORGANISM: Artificial Sequence
<220> FEATURE:
<223> OTHER INFORMATION: PCR product glycalwoTAAUR -continued

<400> SEQUENCE: 26

```
atggattact acagaaaata tgcagctatc tttctggtca cattgtcggt gtttctgcat      60
gttctccatt ccgctcctga tgtgcaggat tgcccagaat gcacgctaca ggaaaaccca     120
ttcttctccc agccgggtgc cccaatactt cagtgcatgg gctgctgctt ctctagagca     180
tatcccactc cactaaggtc caagaagacg atgttggtcc aaaagaacgt cacctcagag     240
tccacttgct gtgtagctaa atcatataac agggtcacag taatgggggg tttcaaagtg     300
gagaaccaca cggcgtgcca ctgcagtact tgttattatc acaaatctaa tagctgtgag     360
ctgaccaa                                                              368
```

<210> SEQ ID NO 27
<211> LENGTH: 227
<212> TYPE: PRT
<213> ORGANISM: Artificial Sequence
<220> FEATURE:
<223> OTHER INFORMATION: synthetic peptide AB-FSH

<400> SEQUENCE: 27

```
Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
                100                 105                 110

Tyr His Lys Ser Asn Ser Cys Glu Leu Thr Asn Ile Thr Ile Ala Ile
            115                 120                 125

Glu Lys Glu Glu Cys Arg Phe Cys Ile Ser Ile Asn Thr Thr Trp Cys
        130                 135                 140

Ala Gly Tyr Cys Tyr Thr Arg Asp Leu Val Tyr Lys Asp Pro Ala Arg
145                 150                 155                 160

Pro Lys Ile Gln Lys Thr Cys Thr Phe Lys Glu Leu Val Tyr Glu Thr
                165                 170                 175

Val Arg Val Pro Gly Cys Ala His His Ala Asp Ser Leu Tyr Thr Tyr
                180                 185                 190

Pro Val Ala Thr Gln Cys His Cys Gly Lys Cys Asp Ser Asp Ser Thr
            195                 200                 205

Asp Cys Thr Val Arg Gly Leu Gly Pro Ser Tyr Cys Ser Phe Gly Glu
        210                 215                 220

Met Lys Glu
225
```

<210> SEQ ID NO 28
<211> LENGTH: 561
<212> TYPE: DNA
<213> ORGANISM: Homo sapiens
<220> FEATURE:
<221> NAME/KEY: misc_feature

```
<222> LOCATION: (1)..(561)
<223> OTHER INFORMATION: cDNA sequence of INF-beta without stop codon

<400> SEQUENCE: 28
atgaccaaca agtgtctcct ccaaattgct ctcctgttgt gcttctccac tacagctctt      60
tccatgagct acaacttgct tggattccta caaagaagca gcaattttca gtgtcagaag     120
ctcctgtggc aattgaatgg gaggcttgaa tactgcctca aggacaggat gaactttgac     180
atccctgagg agattaagca gctgcagcag ttccagaagg aggacgccgc attgaccatc     240
tatgagatgc tccagaacat ctttgctatt ttcagacaag attcatctag cactggctgg     300
aatgagacta ttgttgagaa cctcctggct aatgtctatc atcagataaa ccatctgaag     360
acagtcctgg aagaaaaact ggagaaagaa gatttcacca ggggaaaact catgagcagt     420
ctgcacctga aagatatta tgggaggatt ctgcattacc tgaaggccaa ggagtacagt      480
cactgtgcct ggaccatagt cagagtggaa atcctaagga cttttactt cattaacaga     540 cttacaggtt acctccgaaa c                                              561

<210> SEQ ID NO 29
<211> LENGTH: 513
<212> TYPE: DNA
<213> ORGANISM: Homo sapiens
<220> FEATURE:
<221> NAME/KEY: misc_feature
<222> LOCATION: (1)..(513)
<223> OTHER INFORMATION: INF-alpha-2B sequence with enterokinase site

<400> SEQUENCE: 29
gacgacgacg acaagtgtga tctgcctcaa acccacagcc tgggtagcag gaggaccttg      60
atgctcctgg cacagatgag gagaatctct cttttctcct gcttgaagga cagacatgac     120
tttggatttc cccaggagga gtttggcaac cagttccaaa aggctgaaac catccctgtc     180
ctccatgaga tgatccagca gatcttcaat ctcttcagca caaggactc atctgctgct     240 tgggatgaga ccctcctaga caaattctac actgaactct accagcagct gaatgacctg     300
gaagcctgtg tgatacaggg ggtgggggtg acagagactc ccctgatgaa ggaggactcc     360
attctggctg tgaggaaata cttccaaaga atcactctct atctgaaaga gaagaaatac     420
agcccttgtg cctgggaggt tgtcagagca gaaatcatga gatcttttc tttgtcaaca     480 aacttgcaag aaagtttaag aagtaaggaa tga                                  513

<210> SEQ ID NO 30
<211> LENGTH: 1074
<212> TYPE: DNA
<213> ORGANISM: Homo sapiens
<220> FEATURE:
<221> NAME/KEY: misc_feature
<222> LOCATION: (1)..(1074)
<223> OTHER INFORMATION: INF-beta/INF-alpha-2B sequence with
      enterokinase site

<400> SEQUENCE: 30
atgaccaaca agtgtctcct ccaaattgct ctcctgttgt gcttctccac tacagctctt      60
tccatgagct acaacttgct tggattccta caaagaagca gcaattttca gtgtcagaag     120
ctcctgtggc aattgaatgg gaggcttgaa tactgcctca aggacaggat gaactttgac     180
atccctgagg agattaagca gctgcagcag ttccagaagg aggacgccgc attgaccatc     240
tatgagatgc tccagaacat ctttgctatt ttcagacaag attcatctag cactggctgg     300
aatgagacta ttgttgagaa cctcctggct aatgtctatc atcagataaa ccatctgaag     360
```

```
acagtcctgg aagaaaaact ggagaaagaa gatttcacca ggggaaaact catgagcagt    420
ctgcacctga aagatatta tgggaggatt ctgcattacc tgaaggccaa ggagtacagt    480
cactgtgcct ggaccatagt cagagtggaa atcctaagga acttttactt cattaacaga    540
cttacaggtt acctccgaaa cgacgacgac gacaagtgtg atctgcctca aacccacagc    600
ctgggtagca ggaggacctt gatgctcctg gcacagatga ggagaatctc tctttttctcc   660 tgcttgaagg acagacatga ctttggattt ccccaggagg agtttggcaa ccagttccaa    720
aaggctgaaa ccatccctgt cctccatgag atgatccagc agatcttcaa tctcttcagc    780
acaaaggact catctgctgc ttgggatgag accctcctag acaaattcta cactgaactc    840
taccagcagc tgaatgacct ggaagcctgt gtgatacagg gggtggggt gacagagact     900 cccctgatga aggaggactc cattctggct gtgaggaaat acttccaaag aatcactctc    960
tatctgaaag agaagaaata cagcccttgt gcctgggagt tgtcagagc agaaatcatg    1020 agatcttttt ctttgtcaac aaacttgcaa gaaagtttaa gaagtaagga atga          1074

<210> SEQ ID NO 31
<211> LENGTH: 1059
<212> TYPE: DNA
<213> ORGANISM: Homo sapiens
<220> FEATURE:
<221> NAME/KEY: misc_feature
<222> LOCATION: (1)..(1059)
<223> OTHER INFORMATION: INF-beta/INF-alpha-2B sequence without
      enterokinase site

<400> SEQUENCE: 31
atgaccaaca agtgtctcct ccaaattgct ctcctgttgt gcttctccac tacagctctt     60
tccatgagct acaacttgct tggattccta caaagaagca gcaattttca gtgtcagaag    120
ctcctgtggc aattgaatgg gaggcttgaa tactgcctca aggacaggat gaactttgac    180
atccctgagg agattaagca gctgcagcag ttccagaagg aggacgccgc attgaccatc    240
tatgagatgc tccagaacat cttttgctatt ttcagacaag attcatctag cactggctgg   300
aatgagacta ttgttgagaa cctcctggct aatgtctatc atcagataaa ccatctgaag    360
acagtcctgg aagaaaaact ggagaaagaa gatttcacca ggggaaaact catgagcagt    420
ctgcacctga aagatatta tgggaggatt ctgcattacc tgaaggccaa ggagtacagt     480
cactgtgcct ggaccatagt cagagtggaa atcctaagga acttttactt cattaacaga    540
cttacaggtt acctccgaaa ctgtgatctg cctcaaaccc acagcctggg tagcaggagg    600
accttgatgc tcctggcaca gatgaggaga atctctcttt tctcctgctt gaaggacaga    660
catgactttg gatttcccca ggaggagttt ggcaaccagt tccaaaaggc tgaaaccatc    720
cctgtcctcc atgagatgat ccagcagatc ttcaatctct tcagcacaaa ggactcatct    780
gctgcttggg atgagaccct cctagacaaa ttctacactg aactctacca gcagctgaat    840
gacctggaag cctgtgtgat acaggggtg ggggtgacag agactcccct gatgaaggag    900
gactccattc tggctgtgag gaaatacttc caaagaatca ctctctatct gaaagagaag    960
aaatacagcc cttgtgcctg ggaggttgtc agagcagaaa tcatgagatc ttttctttg    1020 tcaacaaact gcaagaaag tttaagaagt aaggaatga                          1059
```

METHOD OF PRODUCING RECOMBINANT DNA MOLECULES

CROSS-REFERENCE TO PRIOR APPLICATION

This is a U.S. National Phase Application under 35 U.S.C. §371 of International Patent Application No. PCT/EP2004/006600 filed Jun. 18, 2004, and claims the benefit of U.S. Provisional Patent Applications No. 60/480,581 filed Jun. 20, 2003 and No. 60/493,586 filed Aug. 7, 2003, both of which are incorporated by reference herein. The International Application was published in English on Dec. 29, 2004 as WO 2004/113565 A1 under PCT Article 21(2).

FIELD OF THE INVENTION

The present invention is directed to an improved method for producing by recombinant methods proteins that occur in nature in two or more subunits; more generally, it is applicable to the amplification and subsequent expression of any chimeric DNA molecule that results from the ligation of two or more non-contiguous pieces of DNA.

BACKGROUND OF THE INVENTION

The expression of fusion proteins is well known in the art and it is disclosed for instance in the following patent publications: EP-6694, EP-20290, U.S. Pat. Nos. 4,898,830, 5,452,199, EP-213472, EP-196864, EP-461165.

The manufacture of recombinant proteins of interest (e.g., human) in suitable expression systems is one of the main industrial applications of recombinant DNA technology. If, as is often the case, the protein is unstable in the host cell, it may be advantageous to manufacture the protein of interest in the form of a fusion moiety comprising a protective (or stabilising) protein which will be subsequently processed at a specific predetermined site in order to free the desired protein.

Another reason for making fusion proteins is to increase expression levels and/or to facilitate the purification process by the selection of suitable polypeptide sequences and attachment of one or more of such sequences to the amino- or carboxy-terminal ends of the polypeptide or protein of interest. A further reason for expressing a fusion protein might be that of having the characterizing features of two or more different proteins or subunits in a single chain, thus providing a higher activity/dose ratio of the protein itself, and/or avoiding the extra steps to obtain ligation of two subunits. One of the classical problems associated with the expression of recombinant proteins is that of obtaining a valuable and reliable source of the nucleic acid to be expressed.

One way of addressing this problem is to use an mRNA coding for the protein to be expressed. mRNA is however not always easily found under natural conditions. For example, in the case of beta-chain human follicle stimulating hormone (FSH), the corresponding mRNA can be found only in human pituitary cells and only in minute quantities. To be useable, this mRNA must be taken from the human pituitary cells immediately after death.

An alternative is to obtain the coding sequences of interest from genomic DNA. This is however a cumbersome and time consuming process as often, large amounts of unwanted DNA material are present in the initial sample which increases the probability of mutations and other errors. The need therefore still exists for an improved process for generating nucleic acid sequences to be used for expressing polypeptides, and in particular for generating nucleic acid sequences to be used for expression of heterologous recombinant fusion polypeptides.

SUMMARY OF THE INVENTION

The present inventors have now found a method that permits the expression of proteins and fusion proteins starting from genomic DNA without at least one of the foregoing disadvantages associated with known methods. This new methodology offers a novel approach to the production of recombinant proteins: the present methodology makes it possible to ligate and amplify encoding pieces of DNA at the desired positions without the use of restriction enzymes. This means that it is possible to use only the exact encoding regions of a desired DNA (i.e. without introns) thus avoiding splicing and/or reducing the formation of non desired amplicons.

An example of the advantages of this new methodology is represented by the expression of the human beta FSH. The gene expressing human beta FSH is over 1500 bases long whereas the corresponding coding region is only 390 bases long. According to the present methodology it is possible to construct an expression construct containing the correct 390 bases DNA sequence without having to use the 1500 bases of the entire gene. It is thus possible to eliminate 1110 extra bases of unwanted and possibly problem causing DNA without using restriction enzymes and without going through the extra steps of isolating mRNA, and generating cDNA. The present invention is thus expedient, inexpensive and less error prone.

With the present methodology it is also possible and relatively simple to design chimeric molecules of DNA expressing the characteristics of two different proteins or protein subunits in a single chain or even expressing only portions of a particular protein responsible for its activity. For example it is possible to express a new protein having FSH activity as well as LH activity. In other words, it is possible to create new proteins with additional, increased or otherwise modified activity. By using small and precise pieces of DNA it is also possible to manipulate the actual active site of a wild-type protein in order to obtain a smaller polypeptide endowed with the same or similar activity; due to its lower size, the new polypeptide might thus be administered to a patient by different administration routes than the wild-type protein (i.e. by inhalation or transdermally or transmucosally rather than by injection) or possess other advantages such as increase yield during recombinant production of the therapeutic protein.

As will become apparent from the following detailed description and from the examples, the present method is based on a series of PCR amplification steps which are initially carried out on two non-contiguous DNA segments X1 and X2 which are thus fused together. The thus obtained polynucleotide (X1X2) is then inserted in a suitable expression vector to express the desired polypeptide in recombinant cells or transgenic animals according to known methods. The polypeptide may be a fusion polypeptide, or a polypeptide identical to a protein that is naturally produced by translation of a cDNA of polynucleotide elements X1 and X2, where X1 and X2 are exon sequences that are not adjacent in the genomic DNA. Additional chimeric polypeptides within the scope of the invention include dual-activity polypeptides, such as luteinizing hormone-follicle stimulating hormone (LH-FSH) or single polypeptide, propolypeptide, or prepropolypeptide wherein the mature protein is LH, FSH, thyroid stimulating hormone (TSH), chorionic gonadotropin (CG), or any other active polypeptide.

In another aspect, the present invention is directed to a chimeric follicle stimulating hormone (FSH) polypeptide having FSH activity but comprising, instead of two separate polypeptide chains (designated α and β in the native molecule), a single fusion polynucleotide segment encoding the α-chain having its 3' end directly fused to the 5' end of the β-chain. The encoded chimeric polypeptide molecule is termed AB-FSH, and has been shown to possess FSH activity. This method of producing a chimeric AB-FSH protein allows for simplified expression of active follicle stimulating hormone, as the complete protein is encoded in a single vector and expressed from a single promoter. The method alloes for easy purification of an active, stable AB-FSH fusion protein, free from isolated beta-FSH and/or alpha-FSH chains.

Preferably, AB-FSH is expressed with the signal sequence for the α-chain to direct secretion of the fusion protein out of the expressing cell and facilitate its subsequent purification. The signal sequence would be cleaved off in post-translational modification. Alternately, the signal sequence of the β chain can be used 5' to the α chain, or the signal sequence of the α chain can be used 5' to the β chain.

BRIEF DESCRIPTION OF THE DRAWINGS

In FIG. 3, the symbol:

● represents Taq DNA polymerase;

→ indicates the directionality of Taq DNA polymerase processivity; and

▭ and ■ represent nucleotides released from Species B by the 5'-3' exonuclease activity of Taq DNA polymerase.

Figure 4:
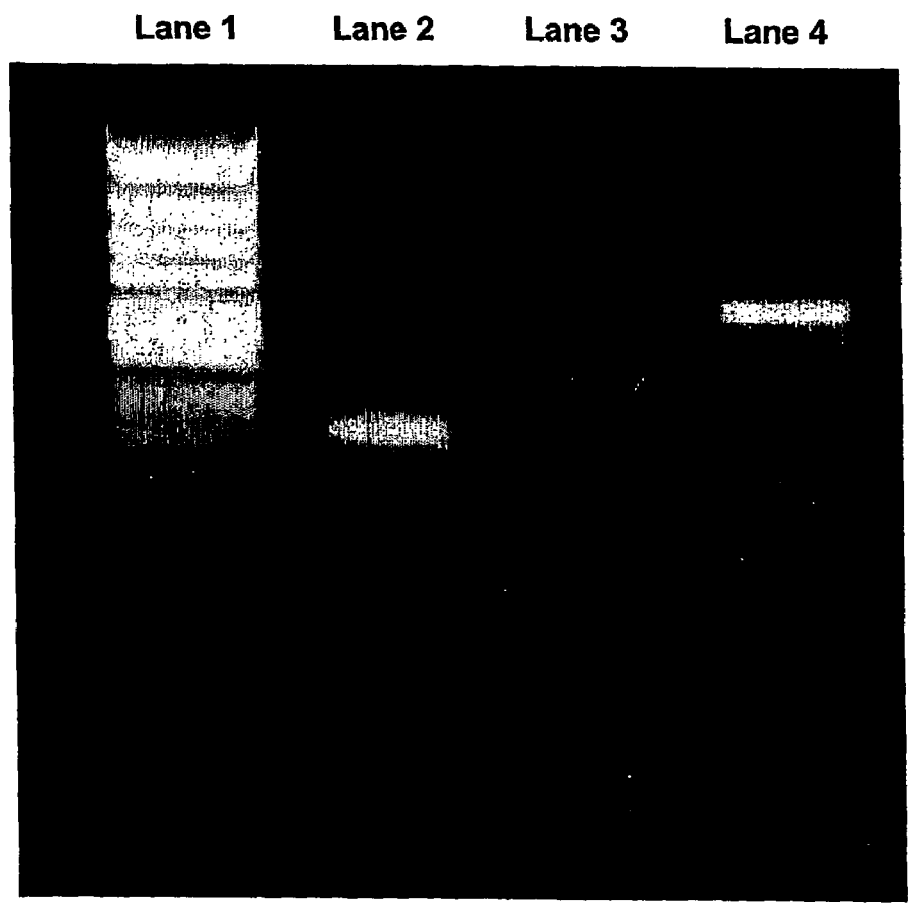

FIG. 4 is a photograph of an agarose gel showing the successful PCR amplification of the X1 beta-FSH PCR product (lane 2), the X2 beta-FSH PCR product (lane 3), and the X1X2 beta-FSH PCR product (lane 4). Lane 1 is the ØX/Hinc II MK13a (HT Biotechnology Ltd., Cambridge, UK) molecular weight markers.

Figure 5:
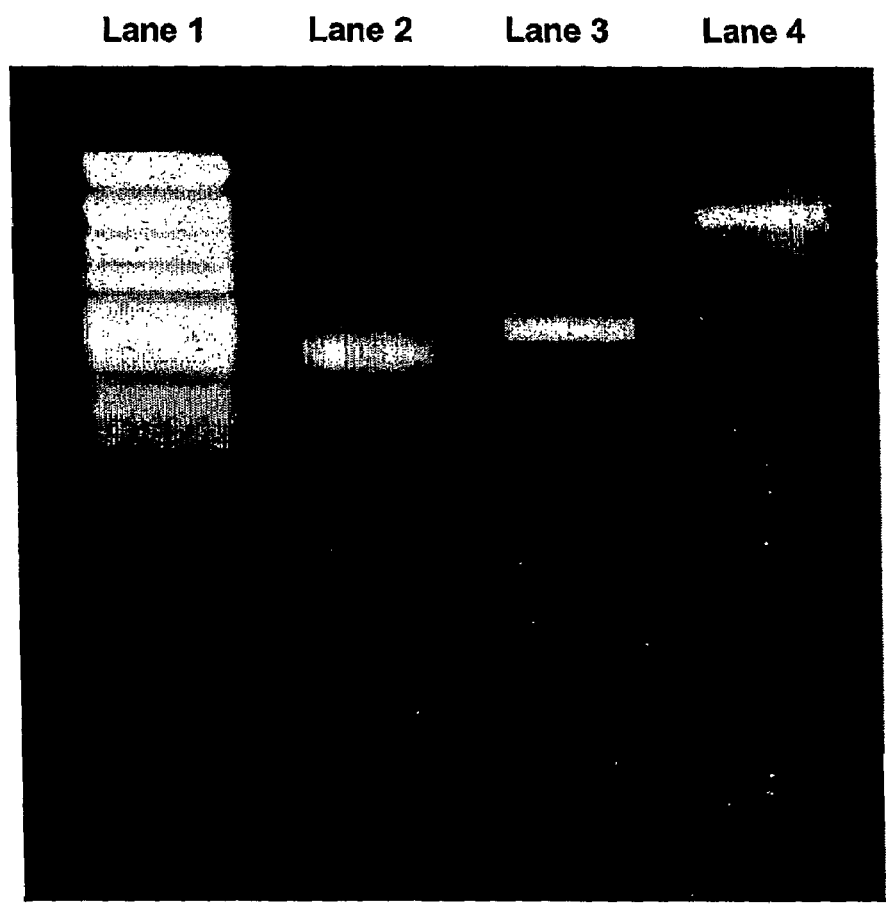

FIG. 5 is a photograph of an agarose gel showing the successful PCR amplification of the S-FSH-B PCR product (lane 2), the glycalA RT-PCR product (lane 3), and the AB-FSH (alpha-beta-FSH) PCR product (lane 4). Lane 1 is the ØX/Hinc II MK13a (HT Biotechnology Ltd., Cambridge, UK) molecular weight markers.

DETAILED DESCRIPTION OF THE INVENTION

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Definitions

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

The term "gene" means a DNA sequence that codes for or corresponds to a particular sequence of amino acids which comprise all or part of one or more proteins or enzymes, which DNA sequence may or may not include regulatory DNA sequences (such as promoter sequences) and untranslated sequences (such as the 5' untranslated region, 3' untranslated region, and introns). Some genes, which are not structural genes, may be transcribed from DNA to RNA, but are not translated into an amino acid sequence.

In discussing the structure of particular double-stranded DNA molecules, sequences may be described herein according to the normal convention of defining the sequence in the 5' to 3' direction along the nontranscribed strand of DNA (i.e., the strand having a sequence homologous to the transcribed mRNA, also known as the sense strand or the "forward" strand). The organization of other DNA sequences relative to the particular double-stranded DNA molecule may be described herein according to the normal convention wherein sequences at the 5' end of the particular double-stranded DNA are "upstream" sequences (UR), and sequences at the 3' end of the particular double-stranded DNA are "downstream" (DR) sequences. Note however, that the present method is valid for the amplification of both the reference sense ("forward") strand and of its complementary antisense (or "reverse") strand.

In discussing the structure of a particular single stranded polynucleotide (such as an oligonucleotide PCR primer or an isolated strand of a double stranded DNA molecule), sequences are described herein according to the normal convention of defining the sequence in the 5' to 3' direction, which 5' end represents the terminal phosphate end of said single stranded polynucleotide and which 3' end represents the terminal hydroxy end of said single stranded polynucleotide. In particular, a "forward" primer is an oligonucleotide which hybridizes to the 3' end of the antisense (or "reverse") strand in order to direct 5'-3' polymerization of the complementary sense (or "forward" strand). Conversely, a "reverse" primer is an oligonucleotide which hybridizes to the 3' end of the sense (or "forward") strand in order to direct 5'-3' polymerization of the complementary antisense (or "reverse") strand.

By "expression construct", "expression vector" or "construct" is meant a nucleic acid comprising a target nucleic acid sequence or sequences whose expression is desired, operably linked to sequence elements which provide for the proper transcription and translation of the target nucleic acid sequence(s) within the chosen host cells. Such sequence elements may include, for example, a promoter, a signal sequence for secretion, and polyadenylation signal. The expression construct", "expression vector" or "construct" further comprises "vector sequences". By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes. The expression constructs of the invention can be introduced into a host cell, so as to transform the host and promote expression (e.g. transcription and translation) of the introduced target nucleic acid sequence.

A "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

A sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

By "host cell" is meant a cell which has been transfected or transformed with one or more expression constructs of the invention. Such host cells include prokaryotic and eukaryotic cells. Preferred eukaryotic cells for use in the present invention are in vitro cultured mammalian cells, such as COS cells and CHO cells. The term host cells also encompasses transformed cells found in vivo, such as in a transgenic mammal.

By "transfection" or "transformation" is meant the process of introducing one or more of the expression constructs of the invention into a host cell by any of the methods well established in the art, including (but not limited to) microinjection, electroporation, liposome-mediated transfection, calcium phosphate-mediated transfection, or virus-mediated transfection. A host cell into which an expression construct of the invention has been introduced by transfection or transformation is "transfected" or "transformed".

Amplification of the Chimeric Polynucleotide X1X2

The present inventors have discovered a method for amplifying a chimeric polynucleotide (X1X2) comprising two non-contiguous nucleotide segments of interest, X1 and X2. In one embodiment, the X1 and X2 sequences are derived from sequences that encode distinct proteins, such that the X1X2 sequence encodes a fusion protein. In another embodiment, the X1 and X2 sequences are derived from sequences that encode a single protein. For example, X1 and X2 may represent the sequences of two exons of a gene, which are not adjacent in the genomic sequence of the gene (e.g. due to separation by introns or possibly other exons or a portion of an exon), but which are adjacent in the transcribed mRNA of the gene (e.g. due to splicing to remove intervening sequences). In this case, the method of the present invention allows for the direct production of the joined X1X2 sequence, wherein X2 is immediately 3' to X1, without the necessity of isolating spliced RNA, making cDNA, or performing complex restriction digestion and ligation of genomic DNA sequences.

The two nucleotide segments of interest, X1 and X2, can be obtained from a nucleic acid mixture comprising a nucleic acid molecule which includes X1 and a nucleic acid molecule which includes X2. Alternatively, the two nucleotide segments of interest, X1 and X2, are included in the same nucleic acid molecule but they are not contiguous. For example, the nucleic acid molecule may be genomic DNA. Preferably, the nucleic acid molecules are be derived from a mammal, particularly a human.

Figure 1:
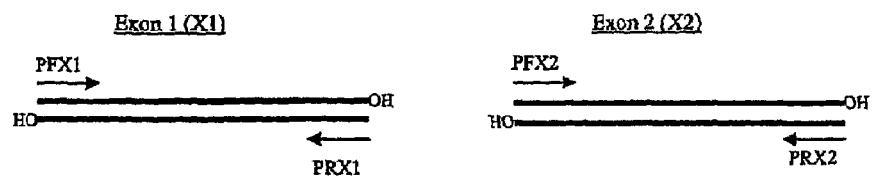
FIG. 1 is a schematic representation of two pieces of starting material (double-stranded polynucleotide segments) and the associated primers used in the initial PCR reactions to amplify starting materials. PFX1 is a forward PCR primer for Exon 1; PRX1 is a reverse PCR primer for Exon 1; "OH" and "HO" represent 3' terminal hydroxy groups of the double stranded DNA; PFX2 is a forward PCR primer for Exon 2; and PRX2 is a reverse PCR primer for Exon 2.

In one embodiment of the present invention, the method comprises four different PCR reactions:

In the first reaction a first nucleic acid segment X1 is made and amplified with a first primer set, which primer set comprises (i) a first primer, PFX1 (which stands for "primer forward for X1") that hybridizes to the 3' end of one strand of the X1 sequence and (ii) a second primer, PRX1 (which stands for "primer reverse for X1") that hybridizes to 3' end of the complementary strand of the X1 sequence (FIG. 1). The amplified X1 PCR product may be isolated by any suitable method (as described, for example, in "Molecular Cloning: A Laboratory Manual." 2$^{nd}$ Edition. Sambrook, et al. Cold Spring Harbor Laboratory: 1989, "A Practical Guide to Molecular Cloning" Perbal: 1984, and "Current Protocols in Molecular Biology" Ausubel, et al., eds. John Wiley & Sons: 1989; commercially available kits include, e.g., the QIAquick PCR Purification Kit and the QLAEX II Gel Extraction Kit, both from Qiagen)

In the second reaction, a second nucleic acid segment X2 is made and amplified with a second primer set, which second primer set comprises (i) a second forward primer, PFX2, that hybridizes to the 3' end of one strand of the X2 sequence and (ii) a second reverse primer, PRX2, that hybridizes to the 3' end of the complementary strand of the X2 sequence. The amplified X2 product can be isolated or purified using any suitable method.

In the third PCR reaction (FIG. 2), an intermediate molecule X1UR or DRX2 is made and amplified. X1UR comprises the entire first nucleic acid segment of X1 and a relatively small 5' segment of X2, wherein the 3' end of X1 is fused to the 5' segment of X2. DRX2 comprises the entire first nucleic acid segment of X2 and a relatively small 3' segment of X1, wherein the 5' end of X2 is fused to the 3' segment of X1. This step is carried out with a third primer set. For X1UR, the third primer set comprises (i) PFX1 and (ii) a fusion primer PRX1-PFX2', which fusion primer has the nucleotide sequence of PRX1 followed immediately at its 3' end by the sequence of the complement of PFX2 (designated as PFX2'). For DRX2, the third primer set comprises (i) a fusion primer PRX1'-PFX2, which fusion primer has the nucleotide sequence of the complement of PRX1 (designated as PRX1')

attached to the 5' end of the forward primer PFX2, and (ii) the primer PRX2. Either intermediate can be isolated or purified using any suitable method.

In the fourth reaction (FIG. 3), the desired polynucleotide X1X2 is finally made and amplified. This PCR reaction relies on the fact that for many commercially available sources of Taq DNA polymerase, the Taq enzyme possesses both 5'-3' DNA polymerase activity and 5'-3' exonuclease activity at certain temperatures.

In one embodiment of this fourth reaction, the following reagents are used: the X1UR amplified product, the X2 amplified product and the primers PFX1 and PRX2. In this reaction, both X1UR and X2 serve as templates for PCR using primers PFX1 and PRX2. The templates are annealed to from two species of significance here: Species A and Species B.

Species A consists of the forward (5'-3') strand of X1UR and the reverse (3'-5') strand of X2, with the two strands annealed via the complementary X2-derived sequences of the UR region of X1UR and the 3' end of the reverse strand of X2. Although neither primer binds to Species A, the Taq polymerase will extend the 3' ends of the annealed overlap region to produce the double stranded species X1X2.

Species B consists of the reverse (3'-5') strand of X1UR and the forward (5'-3') strand of X2, with the two strands annealed via the complementary X2-derived sequences of the UR region of X1UR and the 5' end of the forward strand of X2. Both primers bind to this species. The 3' ends of the annealed primers are then extended by the 5'-3' polymerase activity of the Taq polymerase. Both strands of the final X1X2 product will be intact, because as each primer is extended on its template in the 5'-3 direction, the original annealed strand (reverse of X1UR or forward of X2) is removed by the 5'-3' exonuclease activity of the Taq polymerase. In other words, there will be no "nick" in the strand where the extension product of PRX2 "meets" the 5' end of the reverse strand of X1UR because the latter will be removed by the Taq enzyme, while the (newly synthesized) forward strand of X1X2 will serve as a template for the remainder of the extension product of PRX2 to be built. The same process is at work to result in the full forward strand of X1X2: when the extension product of primer PRX1 "meets" the 5' end of the forward strand of X2, this strand is removed by the Taq enzyme, while the (newly synthesized) reverse strand of X1X2 will serve as a template for the remainder of the extension product of PFX1 to be built.

In an alternate embodiment of this fourth reaction, the following reagents are used: the DRX2 amplified product, the X1 amplified product, and the primers PFX1 and PRX2. In this reaction, both DRX2 and X1 serve as templates for PCR using primers PFX1 and PRX2. This version of the fourth PCR reaction, wherein annealing to form Species A and Species B is mediated by the complementary X1-sequences of X1 and the DR region of DRX2, is analogous to the embodiment described immediately above and also encompassed by the present specification.

In yet another embodiment of this fourth reaction, the following reagents are used: the X1UR amplified product, the DRX2 amplified product, and the primers PFX1 and PRX2. In this reaction, both X1UR and DRX2 serve as templates for PCR using primers PFX1 and PRX2. This version of the fourth PCR reaction, wherein annealing to form Species A and Species B is mediated both by the complementary X2-sequences of the UR region of X1UR and the 5' end of the forward strand of X2 and by the the complementary X1-sequences of X1 and the DR region of DRX2, is analogous to the embodiment described immediately above and also encompassed by the present specification.

It will be understood that for extension of Species A no oligonucleotide primers are necessary. Therefore, the forgoing directions to employ a polymerase that also acts as an exonuclease pertain to amplification of Species B. In practice, however, both extension of Species A and Species B will take place in the same reaction mixture for reasons of efficiency and convenience, so the same enzyme will be used for both.

In other embodiments of the present invention, the method comprises fewer than four different PCR reactions.

For example, the present method does not require that both (or all) of the starting DNA segments X1 and X2 be PCR amplified or isolated. Therefore, the intermediate products X1UR and/or DRX2 may be generated directly from the primary template sequences (e.g. genomic DNA or cDNA) without first performing a PCR to generate X1 or X2. For example, the primer PFX1 and the hybrid primer PRX1-PFX2' may be used to amplify X1UR directly from genomic DNA. Similarly, the primer PRX2 and the hybrid primer PRX1'-PFX2 may be used to amplify DRX2 directly from genomic DNA. Starting from amplified or isolated X1 and X2 sequences, however, makes the subsequent amplification steps more efficient.

The segment X2 should be amplified or isolated when it is combined with X1UR to assemble the chimeric DNA molecule X1X2. Similarly, the segment X1 should be amplified or isolated when it is combined with DRX2 to assemble the chimeric DNA molecule X1X2.

According to the preferred embodiment (hereinafter referred to as "Strategy #2"), the present invention is directed to a method for making a polynucleotide (X1X2) comprising two nucleotide segments of interest, X1 and X2, wherein X2 in X1X2 is immediately 3' to X1, from a nucleic acid molecule including X1 and the same or a different nucleic acid molecule including X2, wherein if X1 and X2 originate on the same molecule, they are not contiguous, the method comprising:
 (a) amplifying a first double stranded nucleic acid segment X1, which segment comprises a sense and an antisense nucleic acid strand, with a first primer set, which primer set comprises (i) a forward primer, PFX1, which hybridizes to the 3' end of the antisense strand of X1 and (ii) a reverse primer, PRX1, which hybridizes to the 3' end of the sense strand of X1;
 (b) amplifying a second double stranded nucleic acid segment, X2, which segment comprises a sense and an antisense nucleic acid strand, with a second primer set, which second primer set comprises (i) a forward primer, PFX2, which hybridizes to the 3' end of the antisense strand of X2 and (ii) a reverse primer, PRX2, which hybridizes to the 3' end of the sense strand of X2;
 (c) isolating the X1 and X2 products of steps (a) and (b)
 (d) performing PCR in a single reaction vessel, said vessel comprising the isolated X1 and X2 products of step (c) in stoichiometric amounts and primers PFX1, PRX2, and a fusion primer, which fusion primer has the nucleotide sequence of PRX1 preceded at its 5' end by the sequence of the complement of PFX2, said PFX2 complement termed PFX2', wherein PCR performed in this single vessel results in amplification of an intermediate double stranded polynucleotide X1UR, which intermediate comprises a sense and an antisense nucleic acid strand, and which comprises the double stranded nucleic acid segment X1 and a 5' double stranded nucleic acid segment of X2, wherein the 3' end of X1 is fused to the 5' segment of X2, and wherein said reaction also results in amplification of the X1UR intermediate to make X1X2 by denaturing and annealing X1UR and X2 to form annealed species and then extending and amplifying said annealed species using DNA polymerase possessing both 5'-3' polymerase activity and 5'-3' exonuclease activity and primers PFX1 and PRX2.

Alternatively, step (d) can be carried out by performing PCR in a single reaction vessel, said vessel comprising the isolated X1 and X2 products of step (c) in stoichiometric amounts and primers PRX1, PFX2, and a fusion primer, which fusion primer has the nucleotide sequence of PFX2 preceded at its 5' end by the sequence of the complement of PRX1, said PRX1 complement termed PRX1', wherein PCR performed in this single vessel results in amplification of an intermediate double stranded polynucleotide DRX2, which intermediate comprises a sense and an antisense nucleic acid strand, and which comprises the double stranded nucleic acid segment X2 and a 3' double stranded nucleic acid segment of X1, wherein the 5' end of X2 is fused to the 3' segment of X1, and said reaction also results in amplification of the DRX2 intermediate to make X1X2 by denaturing and annealing DRX2 and X1 to form annealed species and then extending and amplifying said annealed species using DNA polymerase possessing both 5'-3' polymerase activity and 5'-3' exonuclease activity and primers PRX1 and PFX2.

It will be understood that the method of the present invention may be used to further attach additional sequences (X3) to the chimeric molecule X1X2. For example, where DNA pieces X1X2 and X3 are to be assembled into the polynucleotide X1X2X3, the segment X1X2 would also have an extension complementing the 5' end of X3 if the UR approach is used (as apposed to the DR approach, where X1X2 would be joined to the segment X3, which has an extension complementing the 3' end of X1X2).

The foregoing methods are not limited to making nucleic acid sequences that encode chimeric proteins, or to assembling nucleic acid sequences that encode multi-exon proteins from genomic source DNA. Any two or more polynucleotide segments can be fused, including restriction fragments from one or more DNA molecules. The foregoing method can be easily adapted to produce polynucleotides comprising three or more noncontiguous or heterologous nucleic acid molecules, or segments of such molecules Suitable Taq polymerases that have the combined polymerase/exonuclease activity are commercially available. See, e.g., Pfu DNA polymerase (# M7741 or # M7745); Tth DNA polymerase (# M2101 or # M2105); Tfl DNA polymerase (# M1945 or # M1945), all available from Promega Corporation, Madison Wis., USA.

The newly amplified polynucleotide of interest X1X2 can thus be isolated by means of standard methodologies and can be inserted into a suitable expression system to provide expression of the corresponding fusion polypeptide.

Expression Constructs

The expression constructs of the invention contain the amplified polynucleotide sequence operably linked to elements necessary for proper transcription and translation of the amplified sequences within the chosen host cells, including a promoter, a translation initiation signal ("start" codon), a translation termination signal ("stop" codon) and a polyadenylation signal. The expression constructs may comprise additional sequences that modify expression of the amplified sequences, including internal ribosome entry sites (IRES), enhancers, response elements, suppressors, signal sequences, and the like.

The promoter sequences may be endogenous or heterologous to the host cell, and may provide ubiquitous (i.e., expression occurs in the absence of an apparent external stimulus and is not cell-type specific) or tissue-specific (also known as cell-type specific) expression.

Promoters which may be used to control gene expression include, but are not limited to, cytomegalovirus (CMV) promoter (U.S. Pat. Nos. 5,385,839 and 5,168,062), the SV40 early promoter region (Benoist and Chambon, Nature 1981, 290:304-310), the promoter contained in the 3' long terminal repeat of Rous sarcoma virus (Yamamoto, et al., Cell 1980, 22:787-797), the herpes simplex virus (HSV) thymidine kinase promoter/enhancer (Wagner et al. Proc. Natl. Acad. Sci. USA 1981; 82:3567-71), and the herpes simplex virus LAT promoter (Wolfe, et al. Nature Genetics 1992; 1:379-384), the regulatory sequences of the metallothionein gene (Brinster et al., Nature 1982, 296:39-42); prokaryotic expression vectors such as the beta-lactamase promoter (Villa-Komaroff, et al., Proc. Natl. Acad. Sci. USA 1978, 75:3727-3731), or the tac promoter (DeBoer, et al., Proc. Natl. Acad. Sci. USA 1983, 80:21-25); see also "Useful proteins from recombinant bacteria" in Scientific American 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; the human beta-actin promoter (Gunning, et al. Proc. Natl. Acad. Sci USA 1987; 84:4831-4835), the glucocorticoid-inducible promoter present in the mouse mammary tumor virus long terminal repeat (MMTV LTR; Klessig, et al. Mol. Cell Biol. 1984; 4:1354-1362), the long terminal repeat sequences of Moloney murine leukemia virus (MuLV LTR; Weiss, et al. RNA Tumor Viruses. (Cold Spring Harbor Laboratory, Cold Spring Harbor, N.Y.: 1985).

The expression constructs further comprise vector sequences that facilitate the cloning and propagation of the expression constructs. A large number of vectors, including plasmid and fungal vectors, have been described for replication and/or expression in a variety of eukaryotic and prokaryotic host cells. Standard vectors useful in the current invention are well known in the art and include (but are not limited to) plasmids, cosmids, phage vectors, viral vectors, and yeast artificial chromosomes. The vector sequences may contain a replication origin for propagation in *E. coli*; the SV40 origin of replication; an ampicillin, neomycin, or puromycin resistance gene for selection in host cells; and/or genes (e.g., dihydrofolate reductase gene) that amplify the dominant selectable marker plus the gene of interest. Prolonged expression of the encoded target-reporter fusion in in vitro cell culture may be achieved by the use of vectors sequences that allow for autonomous replication of an extrachromosomal construct in mammalian host cells (e.g., EBNA-1 and oriP from the Epstein-Barr virus).

For example, a plasmid is a common type of vector. A plasmid is generally a self-contained molecule of double-stranded DNA, usually of bacterial origin, that can readily accept additional foreign DNA and which can readily be introduced into a suitable host cell. A plasmid vector generally has one or more unique restriction sites suitable for inserting foreign DNA. Examples of plasmids that may be used for expression in prokaryotic cells include, but are not limited to, pBR322-derived plasmids, pEMBL-derived plasmids, pEX-derived plasmids, pBTac-derived plasmids, and pUC-derived plasmids.

A number of vectors exist for expression in yeast. For instance, YEP24, YIP5, YEP51, YEP52, pYES2, and YRP17 are cloning and expression vehicles useful in the introduction of genetic constructs into *S. cerevisiae* (see, e.g., Broach, et al. "Experimental Manipulation of Gene Expression." ed. M. Inouye (Academic Press: 1983)). These vectors can replicate in *E. coli* due the presence of the pBR322 ori, and in *S. cerevisiae* due to the replication determinant of the yeast 2 micron plasmid.

A number of expression vectors exist for expression in mammalian cells. Many of these vectors contain prokaryotic sequences to facilitate the propagation of the vector in bacteria, and one or more eukaryotic transcription regulatory sequences that cause expression in eukaryotic cells. The pcDNAI/amp, pcDNAI/neo, pRc/CMV, pSV2gpt, pSV2neo, pSV2-dhfr, pTk2, pRSVneo, pMSG, pSVT7, pkoneo, and pHyg derived vectors are examples of mammalian expression vectors suitable for transfection of eukaryotic cells. Some of these vectors are modified by the addition of sequences from bacterial plasmids, such as pBR322, to facilitate replication and drug resistance selection in both prokaryotic and eukaryotic cells. Derivatives of viruses such as the bovine papilloma virus (BPV-1), or Epstein-Barr virus (pHEBo, pREP-derived and p205) may be used for transient expression of proteins in eukaryotic cells. A baculovirus expression system (see, e.g., "Current Protocols in Molecular Biology." eds. Ausubel et al. (John Wiley & Sons: 1992)) may also be used. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

For other suitable expression systems for both prokaryotic and eukaryotic cells, as well as general recombinant procedures, see "Molecular Cloning A Laboratory Manual. $2^{nd}$ Edition." Sambrook, et al. (Cold Spring Harbor Laboratory Press: 1989) Chapters 16 and 17.

The expression constructs of the invention may be transfected or transformed into eukaryotic or prokaryotic host cells in vitro. Preferred in vitro host cells are mammalian cell lines, such as COS cells and CHO cells. Protocols for in vitro culture of mammalian cells are well established in the art [see for example, *Animal Cell Culture: A Practical Approach* $3^{rd}$ *Edition*. J. Masters, ed. Oxford University Press and *Basic Cell Culture* $2^{nd}$ *Edition*. Davis, J. M. ed. Oxford University Press (2002)]. Techniques for transfection and transformation are well established in the art and may include electroporation, microinjection, liposome-mediated transfection, calcium phosphate-mediated transfection, or virus-mediated transfection [see for example, *Artificial self-assembling systems for gene delivery*. Felgner, et al., eds. Oxford University Press (1996); Lebkowski, et al. Mol Cell Biol 1988 8(10): 3988-3996; "Molecular Cloning: A Laboratory Manual." $2^{nd}$ Sambrook, et al. Cold Spring Harbor Laboratory: 1989; and "Current Protocols in Molecular Biology" Ausubel, et al., eds. John Wiley & Sons: 1989).

Production of Biologically Active Chimeric Proteins

According to a preferred aspect of the invention, the present method is used to produce a polynucleotide X1X2 which encodes a biologically active polypeptide E1E2, wherein E1 is the polypeptide sequence encoded by X1 and E2 is the polypeptide sequence encoded by X2.

According to another aspect of the present invention the two nucleotide segments X1 and X2 are two exons which are both present in the human genome and wherein each encodes one of two fragments of a biologically active protein.

In one example, X1 and X2 encode the two exons of the beta subunit of FSH.

In another example, X1 and X2 encode two subunits of a multi-subunit protein, the alpha-subunit and beta-subunit of FSH. Therefore, according to a further aspect of the present invention the polynucleotide (X1X2) encodes a single polypeptide having the activity of chorionic gonadotropin (CG), luteinizing hormone (LH), follicle stimulating hormone (FSH) or thyroid stimulating hormone (TSH); or encodes a single polypeptide having the activity of more than one of these hormones (e.g., activity of both LH and FSH).

Alternatively, the polynucleotide (X1X2) may encode a pre-protein E1E2, wherein the segment E1 represents a fusion partner, as for instance a signal sequence, and E2 is a biologically active mature polypeptide. The signal sequence may be the natural signal sequence of E2 or a different signal sequence. The objective would be to facilitate secretion of the mature E2.

For example we can produce the β subunit of FSH consisting of segments X1 and X2. Alternatively, we can produce any other chimeric polypeptide by using heterologous segments of DNA fused together. So the chimeric protein will have properties of both the constituent polypeptides. New and unique molecules can thus be generated.

As it will be apparent from the examples, which relate to the expression of the beta-subunit of hFSH and to the expression of a chimeric protein containing both the alpha and beta subunits of FSH (termed AB-FSH), the method according to the present invention can be carried out using any two (or more) non contiguous DNA segments. If additional segments are used, additional PCR steps will be necessary, as a person of ordinary skill will readily appreciate.

EXAMPLES

The present invention is next described by means of the following examples. However, the use of these and other examples anywhere in the specification is illustrative only, and in no way limits the scope and meaning of the invention or of any exemplified form. Likewise, the invention is not limited to any particular preferred embodiments described herein. Indeed, many modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Example 1

Assembly of Beta-FSH Expression Constructs using a Novel PCR Methodology

The sequence of the genomic DNA encoding the β subunit of human FSH is at Genbank Accession # AH003599. The cDNA sequence of the β subunit of human FSH is SEQ ID NO:1. The signal sequence is depicted as SEQ ID NO: 2. Exon 1 has the sequence SEQ ID NO: 3; Exon 2 has the sequence SEQ ID NO: 4. The corresponding amino acid sequence of human β-FSH is at SEQ ID NO: 5. It is to be noted that β FSH exists in various polymorphs of which the present example produces only one. However, any other polymorph could have been easily produced by the present method.

A PCR Amplification of Beta-FSH Encoding Sequences

1. Isolation and Amplification of Two DNA Segments Each Encoding One of Two Exons of Beta-FSH Human genomic DNA was extracted from 50 μl of total blood using the Nucleo Spin Blood Quick Pure kit (Macherey-Nagel GmBH& Co.). The isolated DNA was then dissolved in 100 μl of TB Buffer (DNA solution). 10 μl of this DNA solution was used as template for two independent PCR reactions (5 μl genomic DNA solution per PCR reaction).

The first PCR reaction was performed using primers specific for exon 1 of beta-FSH. The forward primer PFX1 with the sequence (SEQ ID NO: 7) 5'-ATG AAG ACA CTC CAG TTT TTC TTC C-3' corresponds to a segment from position 40 to position 64 in SEQ ID NO: 1. The reverse primer PRX1 with the sequence (SEQ ID NO: 8) 5'-CCT GGT GTA GCA GTA GCC AGC-3' corresponds to the complement of the segment from position 198 to position 178 of SEQ ID NO: 1. This PCR reaction amplifies the product X1, as illustrated at FIG. 1, left scheme.

The second PCR reaction was performed using primers specific for exon 2 of beta-FSH. The forward primer PFX2 with the sequence (SEQ ID NO: 9) 5'-GAT CTG GTG TAT AAG GAC CCA-3' corresponds to the segment from position 199 to position 219 of SEQ ID NO: 1. The reverse primer PRX2 with the sequence (SEQ ID NO: 10) 5'-TTA TTC TTT CAT TTC ACC AAA GG-3' corresponds to the complement of the segment from position 429 to position 407 of SEQ ID NO: 1. This PCR reaction amplifies the product X2, as illustrated at FIG. 1, left scheme.

Each independent PCR reaction contained 5 μl human genomic DNA solution as the template, and the following additional reagents:

1. 10 μl 10×PCR Buffer (Thermophilic DNA Polymerase 10× Buffer, magnesium Free M190G, Promega Madison Wis., USA)
2. 10 μl 25 mmol $MgCl_2$
3. 5 μl dNTPs stock solution containing 10 μmol each of dATP, dTTP, dCTP, and dGTP.
4. 1 μl of 100 pmol/μl forward primer stock dilution
5. 1 μl of 100 pmol/μl reverse primer stock dilution
6. 2 μl TAQ (5 U/μl) (Taq DNA Polymerase in Storage Buffer A, Cat No. Mi865, Promega Madison Wis., USA)
7. 65 μl $H_2O$.

Cycling parameters were as follows: initial denaturation for 2 min at 95° C.; 30 cycles of amplification with each cycle consisting of 30 sec at 94° C., followed by 30 sec at 50° C., and then 1 min at 72° C.; and a final extension for 5 min at 72° C. Cycling was performed using a PTC-100™ programmable Thermal Controller (MJ Research Inc, Watertown, Mass., USA).

Amplification of the X1 and X2 products (beta-FSH exon 1 and exon 2 segments, respectively) by each PCR was confirmed by agarose gel (2% in TAE buffer) electrophoresis for 30 min at 125 mA using the DNA Molecular Weight Marker ØX/Hinc II MK13a (HT Biotechnology Ltd., Cambridge, UK) as control molecular weight markers. The results are shown in FIG. 4 (see Lanes 2 and 3). The X1 and X2 products of the PCR reaction were then purified using the PCR Clean-up Kit (Nucleospin Extract. Cat No. 740590.50).

2. PCR Amplification of the X1UR Intermediate Product:

A PCR reaction was performed on the X1 product (prepared as describe above) as template, using the exon 1 forward primer PFX1 (SEQ ID NO: 7) and a hybrid reverse primer PRX1-PFX2' having the sequence (SEQ ID NO: 11): 5'-<u>TGGGTCCTTATACACCAGATC</u> CCT GGT GTA GCA GTA GCC AGC-3', where the sequence of PRX1 is italicized and the reverse complement of the sequence of PFX2 is underlined.

Figure 2:
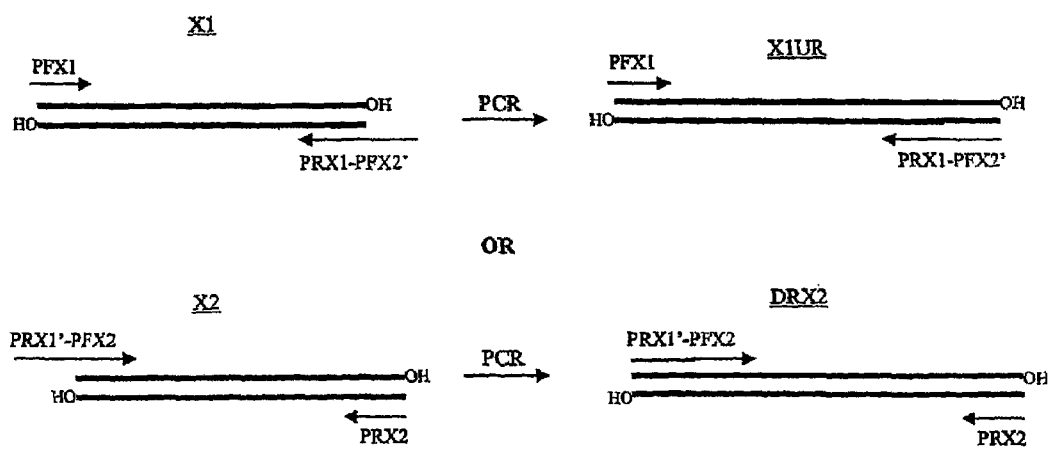
FIG. 2 is a schematic representation of the PCR step to generate an intermediate PCR product in which a portion of the 5' end of X2 is added to the 3' end of the X1 to make X1UR or a portion of the 3' end of the X1 is added to the 5' end of X2 to make DRX2. PRX1-PFX2' is a reverse PCR primer made by combining the PRX1 primer sequence with the complementary sequence of the PFX2 primer (PFX2'); and PRX1'-PFX2 is a forward PCR primer made by combining the complementary sequence of the PRX1 primer (PRX1') with the PFX2 primer sequence.

The PCR reaction mixture contained 1 μl X1 PCR product (exon 1 of beta-FSH: SEQ ID NO: 3) solution as the template, and the additional reagents listed above. Cycling parameters were as follows: initial denaturation for 2 min at 95° C.; 30 cycles of amplification with each cycle consisting of 30 sec at 94° C., followed by 1 min at 50° C., and then 2 min at 68° C.; and a final extension for 10 min at 72° C. Cycling was performed using a PTC-100™ programmable Thermal Controller (MJ Research Inc, Watertown, Mass., USA). This reaction is illustrated at FIG. 2, top scheme.

Amplification of the X1UR intermediate product by PCR was confirmed by agarose gel (2% in TAE buffer) electrophoresis for 30 min at 125 mA using the DNA Molecular Weight Marker ØX/Hinc II MK13a (HT Biotechnology Ltd., Cambridge, UK) as control molecular weight markers. The X1UR PCR product was then purified using the PCR Clean-up Kit (Nucleospin Extract. Cat No. 740590.50) to yield pure DNA in a final volume of 5 μl. Purity and size of the DNA was confirmed by agarose (2% in TAE buffer) electrophoresis for 30 min at 125 mA using the DNA Molecular Weight Marker ØX/Hinc II MK13a (HT Biotechnology Ltd., Cambridge, UK) as control molecular weight markers.

The intermediate X1UR beta-FSH PCR product (SEQ ID NO: 13) consists of the X1 (beta-FSH exon 1; SEQ ID NO:3) sequence extended at its 3' end by the first 21 base pairs of SEQ ID NO:4 (the beta-FSH exon X2 sequence).

3. PCR Amplification of the X1X2 (Exon 1-Exon 2 Beta-FSH) Product

Two different strategies were employed to amplify the product X1X2.

Figure 3:
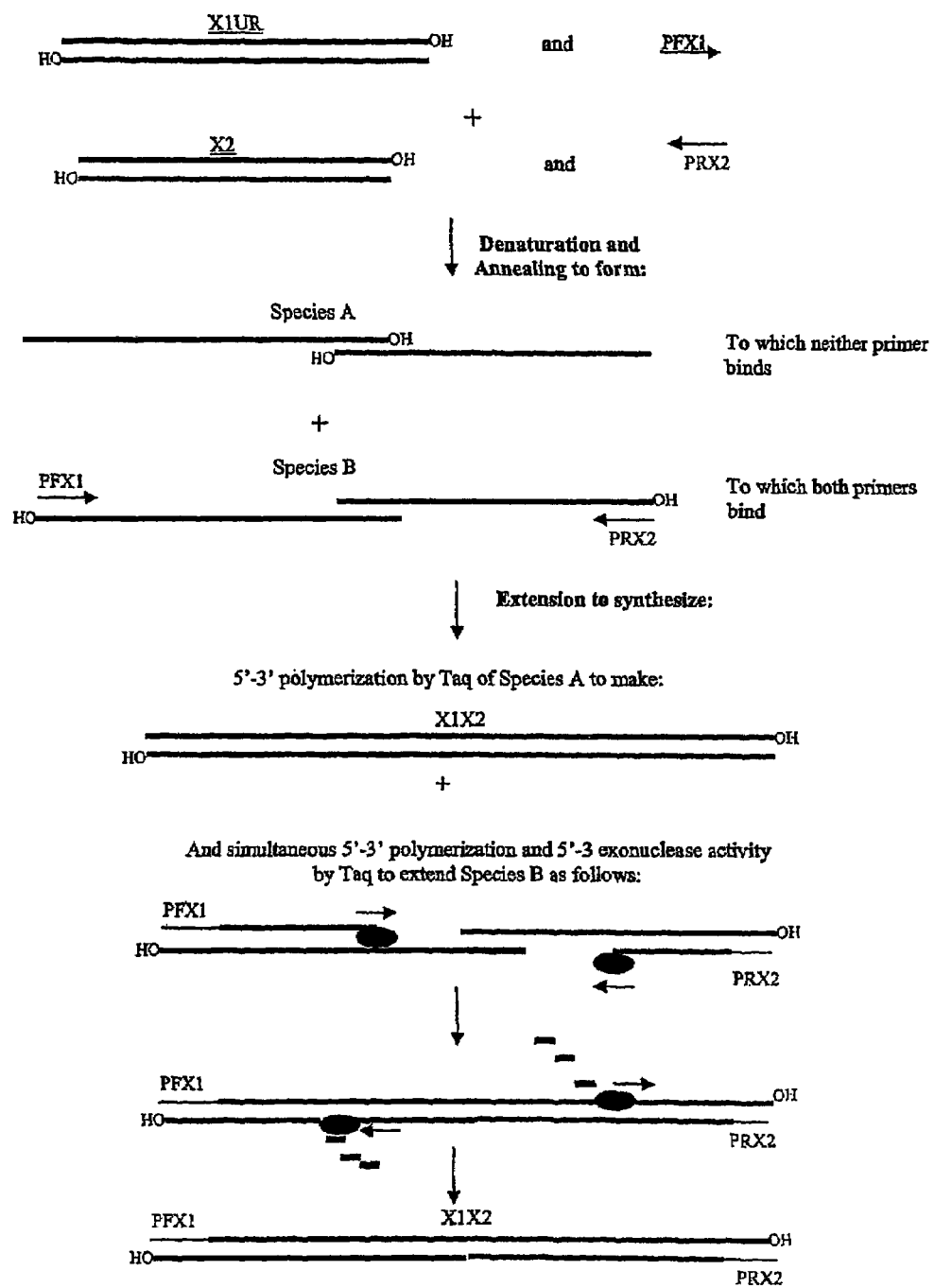
FIG. 3 is a schematic representation of the third PCR reaction step, which illustrates the steps of denaturation of the intermediate product X1UR and the X2 starting material, followed by annealing to form a mix of Species A and Species B, followed by extension in which Species A forms X1X2 by 5'-3' polymerization and Species B forms X1X2 by simultaneous 5'-3' polymerization and 5'-3' exonuclease activity. X1X2 is then further amplified in subsequent rounds of denaturation, annealing and extension. Note that an equivalent mechanism would result in the formation of the X1X2 species from X1 and DRX2 templates using primers PFX1 and PRX2.

Strategy #1:

In the first strategy, illustrated at FIG. 3, a PCR reaction was performed using the exon 1 forward primer PFX1 (SEQ ID NO: 7) and a the exon 2 reverse primer PRX2 (SEQ ID NO: 10). The earlier amplified products X1UR and X2 were the templates for this reaction. This PCR reaction contained the following reagents:

1. 10 μl 10×PCR Buffer (Thermophilic DNA Polymerase 10× Buffer, magnesium Free M190G, Promega Madison Wis., USA)
2. 10 μl 25 mmol $MgCl_2$
3. 5 μl dNTPs stock solution containing 10 μmol each of dATP, dTTP, dCTP, and dGTP.
4. 1 μl X1UR intermediate PCR product (SEQ ID NO: 13)
5. 1 μl X2 PCR product (exon 2 of beta-FSH: SEQ ID NO: 4)
6. 1 μl of 100 pmol/μl PFX1 (beta-FSH exon 1 forward primer (SEQ ID NO: 7)) stock dilution
7. 1 μl of 100 pmol/μl PRX2 (beta-FSH exon 2 reverse primer (SEQ ID NO: 10)) stock dilution
8. 2 μl TAQ (5 U/μl) (Taq DNA Polymerase in Storage Buffer A, Cat No. Mi865, Promega Madison Wis., USA)
9. 65 μl $H_2O$ Cycling parameters were as follows: initial denaturation for 2 min at 95° C.; 30 cycles of amplification with each cycle consisting of 30 sec at 94° C., followed by 1 min at 50° C., and then 2 min at 68° C.; and a final extension for 10 min at 72° C. Cycling was performed using a PTC-100™ programmable Thermal Controller (MJ Research Inc, Watertown, Mass., USA).

Amplification of the X1X2 product by this PCR reaction was confirmed by agarose (2% in TAE buffer) electrophoresis performed as described above. The results are shown in FIG. 4 (see Lane 4). The product of this PCR reaction was then purified using the PCR Clean-up Kit (Nucleospin Extract. Cat No. 740590.50) to yield pure DNA in a final volume of 50 μl. Purity and size of the DNA was confirmed by agarose (2% in TAE buffer) electrophoresis performed as described above.

The size of the product was determined by agarose gel electrophoresis (performed as described above) to be about 390 bp. The sequence of this product was confirmed to be the full length coding sequence for beta-FSH, X1X2 (SEQ ID NO: 6; see Genbank Accession # NM_000510), by conventional sequence analysis using the primer PFX1 (beta-FSH exon 1 forward primer (SEQ ID NO: 7)).

Strategy #2:

In an alternate strategy the final X1X2 PCR product was generated by a single three primer PCR using the X1 and X2 products as template. This strategy shortened the cloning process by one PCR step. In this strategy, the primers PRX2, PFX1, and the hybrid reverse primer PRX1-PFX2' were used on the X1 and X2 products as template, thereby amplifying first the X1UR intermediate and then the X1X2 final product in a single PCR reaction. The PCR reaction contained the following reagents:

1. 10 µl 10×PCR Buffer (Thermophilic DNA Polymerase 10× Buffer, magnesium Free M190G, Promega Madison Wis., USA)
2. 10 µl 25 mmol $MgCl_2$
3. 5 µl dNTPs stock solution containing 10 µmol each of dATP, dTTP, dCTP, and dGTP.
4. 2 µl X1 PCR product (SEQ ID NO: 3)
5. 2 µl X2 PCR product (exon 2 of beta-FSH: SEQ ID NO: 4)
6. 1 µl of 100 pmol/µl PRX2 (beta-FSH exon 2 reverse primer (SEQ ID NO: 10)) stock dilution
7. 1 µl of 100 pmol/µl forward primer PFX1 (beta-FSH exon 1 forward primer (SEQ ID NO: 7) stock dilution
8. 1 µl of 100 pmol/µl hybrid reverse primer PRX1-PFX2' (SEQ ID NO: 11) stock dilution
9. 2 µl TAQ (5 U/µl) (Taq DNA Polymerase in Storage Buffer A, Cat No. Mi865, Promega Madison Wis., USA)
10. 65 µl $H_2O$ Cycling parameters were as follows: initial denaturation for 2 min at 95° C.; 30 cycles of amplification with each cycle consisting of 30 sec at 94° C., followed by 1 min at 50° C., and then 2 min at 68° C.; and a final extension for 10 min at 72° C. Cycling was performed using a PTC-100™ programmable Thermal Controller (MJ Research Inc, Watertown, Mass., USA).

Amplification of the X1X2 product by this PCR reaction was confirmed by agarose (2% in TAE buffer) electrophoresis performed as described above. The product of this PCR reaction was then purified using the PCR Clean-up Kit (Nucleospin Extract. Cat No. 740590.50) to yield pure DNA in a final volume of 50 µl. Purity and size of the DNA was confirmed by agarose (2% in TAE buffer) electrophoresis performed as described above.

The size of the product was determined by agarose gel electrophoresis performed as described above) to be about 390 bp. The sequence of this product was confirmed to be the full length coding sequence for beta-FSH, X1X2 (SEQ ID NO: 6; see Genbank Accession # NM_000510), by conventional sequence analysis using the primer PFX1 (beta-FSH exon 1 forward primer (SEQ ID NO: 7)).

Though the result was the same using both PCR strategies, we used the X1X2 product from the Strategy #1 PCR reaction because it yielded a higher quantity and purity of product DNA. However, the second approach is also viable, and has the advantage of proceeding very fast, although it requires stoichiometric amounts of the templates.

4. Addition of Shine-Delgarno and Kozak Sequences to the X1X2 (Exon 1-Exon 2 Beta-FSH) Product A 17 nucleotide sequence was added to the 5' end of the X1X2 (Exon1-Exon2 beta-FSH) PCR product (SEQ ID NO: 6), in order to create Shine-Delgarno and Kozak consensus sequences (SDK), which direct translation of the expressed SDK-X1X2 transcript. The sequence was added by performing a PCR reaction on the X1X2 PCR product using the primer PRX2, the beta-FSH exon 2 reverse primer (SEQ ID NO: 10); and a new forward primer SDK-PFX1 with the sequence 5'-<u>TCGAAGGAGATAGAACCATG</u>A AGA CAC TCC AGT TTT TCT TCC-3' (SEQ ID NO: 12), where the Shine-Delgarno and Kozak consensus sequences are underlined, the sequence of the exon 1 forward primer PFX1 (SEQ ID NO: 7) is in italics, and the "start" codon for translation initiation is in boldface. The PCR reaction contained 1 µl X1X2 (Exon1-Exon2 beta-FSH) PCR product as the template, and the following additional reagents:

1. 10 µl 10×PCR Buffer (Thermophilic DNA Polymerase 10× Buffer, magnesium Free M190G, Promega Madison Wis., USA)
2. 10 µl 25 mmol $MgCl_2$
3. 5 µl dNTPs stock solution containing 10 µmol each of dATP, dTTP, dCTP, and dGTP.
4. 1 µl of 100 pmol/µl SDK-PFX1 primer (SEQ ID NO: 12) stock dilution
5. 1 µl of 100 pmol/µl PRX2 (beta-FSH exon 2 reverse primer (SEQ ID NO:10)) stock dilution
6. 2 µl TAQ (5 U/µl) (Taq DNA Polymerase in Storage Buffer A, Cat No. Mi865, Promega Madison Wis., USA)
7. 65 µl $H_2O$.

Cycling parameters were as follows: initial denaturation for 2 min at 95° C.; 30 cycles of amplification with each cycle consisting of 30 sec at 94° C., followed by 1 min at 50° C., and then 2 min at 68° C.; and a final extension for 10 min at 72° C.

Amplification of the SDK-X1X2 product by this PCR reaction was confirmed by agarose (2% in TAE buffer) electrophoresis performed as described above. The product of this PCR reaction was then purified using the PCR Clean-up Kit (Nucleospin Extract. Cat No. 740590.50) to yield pure DNA in a final volume of 50 µl. Purity and size of the DNA was confirmed by agarose (2% in TAE buffer) electrophoresis performed as described above.

B. Assembly of Beta-FSH Expression Construct

The SDK-X1X2 PCR product was cloned into the pTARGET™ expression vector (Promega) according to manufacturer's instructions (pTARGET™ Mammalian Expression System Technical Manual). This system is based upon ligation directed by annealing of the 3' adenine overhangs on each end of a PCR product (introduced as a natural consequence of Taq polymerase activity) with 5' thymine overhangs on a linearized pTARGET™ expression vector. The ligated pTARGET™ vector was transformed into *E. coli* DH5α.

Transformed *E. coli* DH5α were cultured on solid medium for 24 hours, and then 10 bacterial colonies from each transformation were used to inoculate individual liquid medium cultures. Plasmid DNA was extracted from cultured liquid medium cultures using the JET Quick Plasmid Miniprep Spin Kit/50 (Genomed GmBH, Wielamdstr Bad Oeynhomsen) according to manufacturer's instructions.

Isolated plasmid DNA was then checked for incorporation of the SDK-X1X2 beta-FSH insert by PCR. In this PCR, primers PFX1 (beta-FSH exon 1 forward primer (SEQ ID NO: 7)) and PRX2 (beta-FSH exon 2 reverse primer (SEQ ID NO: 10)) were used to amplify 1 µl of the purified plasmid DNA template. Successful amplification of the X1X2 fragment confirmed successful cloning of the beta-FSH sequences into the pTARGET vector. The resulting expression construct was named pTPKBFSH (pTARGET containing the SDK-X1X2 PCR product insert).

Example 2

Expression of Beta-FSH in Mammalian Cell Culture

The pTPKBFSH (pTargeT containing the SDK-X1X2 beta-FSH insert) expression construct was used for the expression of beta-FSH protein in COS-7L (Invitrogen, catalog No. 11622016), and CHO-S (Invitrogen, catalog No. 11619012) cell lines. The pTPKBFSH construct was transfected into the various cell lines using the LIPOFECTAMINE 2000 (Invitrogen) transfection reagent according to manufacturer's instructions. The expression vector pSV-β-Galactosidase (Promega) was included as a transfection control.

Following transfection, the cells were cultured in a selective medium containing 1000 μg/ml Geneticine for 7 days. Geneticine-resistant cells were transferred in a new culture medium containing Geneticine at 200 μg/ml, and cultured to a cell density of $10^6$ cells/ml. The supernatant of this culture was than tested for the presence of the beta-FSH subunit using the Granulosa Cell Aromatase Bioassay (GAB assay) method for Follicle Stimulating Hormone (Dahl et al. Methods Enzymol 1989; 168:414-422) for detecting bioactive human beta-FSH. This assay quantitates FSH activity based upon stimulation of aromatase activity of granulosa cells, where aromatase activity is measured by radioimmunoassay quantitation of the production of estrogen from an androstenedione precursor. Thus this assay is a functional assay which quantifies the amount of biologically active beta-FSH protein in a test sample.

To derive Granulosa Cells for the GAB assay, intact female Spague-Dawley rats (21-22 days old) were implanted with silastic capsules (10 mm) containing approximately 10 mg diethylstilbestrol (DES) to stimulate granulosa cell proliferation. Four days later, the animals were sacrificed, and the ovaries removed and decapsulated. Follicles of the decapsulated ovaries were punctured with 27-gauge hypodermic needles, and the granulosa cells removed into McCoy's 5a medium (Gibco), supplemented with penicillin/streptomycin (100 U/mL of each) and 2 mM L-glutamine. The cells were pelleted by low speed centrifugation for 5 min, and then washed with fresh medium. Cell viability was estimated by trypan blue staining of a cell aliquot, followed by cell counting using a hemacytometer. The cells were then diluted in medium to a final volume of ~2000-2400 viable cells/ml.

On the day of the assay, fresh GAB assay medium was prepared. The GAB assay medium was: McCoy's 5a medium (Gibco), supplemented with penicillin/streptomycin (100 U/mL of each) and 2 mM L-glutamine, plus 1.25 μM androstenedione (Sigma), 0.125 μM diethylstilbesterol (Sigma); 37.5 ng/mL human chorionic gonadotropin (Sigma: catalog # C-0434), 0.156 mM 1-methyl-3-isobutylxanthine (Sigma), and 1.25 μg/ml insulin (Sigma: catalog # I-1507).

Then 400 μl of GAB assay medium and 60 μL of granulosa cell suspension (~50,000-80,000 viable cells) were added to each well of a 24-well plate. Next, 40 μL of pTPKBFSH-transfected COS or CHO cell supernatant or of various concentrations of positive control recombinant FSH (Organon) were added to each well. The plates were then cultured for 3 days at 37° C. in a humidified 5% $CO_2$ incubator. The supernatant from each well was then harvested, and 10-20 μl of the supernatant assayed for estrogen levels by radioimunnoassay. Estrogen radioimmunoassay was performed using the Spectria RIA kit for estradiol measurement (Orion Diagnostic, Finland), according to the manufacturer's instructions.

For this assay, various concentrations of the positive control recombinant FSH (Organon) were tested and used to calculate a titration curve for FSH activity (recombinant FSH concentration in milliUnits per milliliter, mU/ml, versus estrogen radioimmunoassay values, see Table 1). This control curve was then used to interpolate the amount of beta-FSH activity in the supernatant of pTPKBFSH-transfected COS or CHO cells.

When a 1/1000 dilution of the supernatant from pTPKBFSH-transfected cells was tested in the granulosa assay, 348 pg/ml of estradiol was produced. This value is roughly equivalent to that seen with 25mU/ml of control recombinant FSH. After correcting for the dilution factor of the tested supernatant, this result indicates that the pTPKBFSH-transfected cell lines produce bioactive beta-FSH at a quantity of about 25 Units/ml.

TABLE 1

Calibration curve values for FSH activity

| Concentration of recombinant FSH tested (mU/mL*) | 25 | 50 | 100 | 200 | 400 |
|---|---|---|---|---|---|
| Concentration of estradiol produced (pg/ml) | 322 | 710 | 1900 | 3400 | 4100 |

*According to the manufacturer (Organon), recombinant FSH shows an activity profile of approximately 8000 Units per mg of total recombinant protein.

Example 3

Production and Expression of Chimeric DNA for AB FSH

The human FSH hormone protein is multi-subunit protein composed of an alpha subunit plus a beta subunit. The complete cDNA sequence for the alpha subunit is SEQ ID NO: 14 (Genbank Accession number NM_000735). This example describes the production of an active human FSH protein in which both subunits of the hormone are contained in a single protein chain.

A. Beta-FSH Subunit Encoding Nucleic Acid Sequence

The beta-FSH subunit encoding sequence (X1X2; SEQ ID NO: 6) was prepared as described in Example 1.

B. Alpha-FSH Subunit Encoding Nucleic Acid Sequence mRNA was isolated from human placental tissue using the Oligotex Direct mRNA Mini Kit (Qiagen, Cat. No. 72022) according to manufacturer's instructions. 5 μl of the isolated mRNA was used as template in a reverse transcriptase-polymerase chain reaction (RT-PCR), using the primers HCG-SENT (5'-ATG GAT TAC TAC AGA AAA TAT GCA GCT ATC-3'; SEQ ID NO: 15) and HCG-ANTISENT (5'-TTA AGA TTT GTG ATA ATA ACA AGT ACT GCA G-3'; SEQ ID NO: 16). This RT-PCR reaction was performed using the RT-PCR Kit (Gibco) according to manufacture's instructions. The product of this RT-PCR was named glycalA, and confirmed to represent the complete coding sequence of human alpha-FSH (SEQ ID NO: 17) by 2% agarose gel electrophoresis (performed as described above; see FIG. 5, lane 3) and sequencing performed using the primers HCG-SENT and HCG-ANTISENT.

The glycalA alpha-FSH RT-PCR product was then cloned into the pLenti6/V5 D-TOPO vector using the pLenti6/V5 Directional TOPO cloning kit according to manufacturer's instructions (Invitrogen K4955-10). To facilitate this cloning, the nucleotide sequence CACC was added to the 5' end of the glycalA RT-PCR product via PCR using the primers HCG-SENTCACC (5'-CAC CAT GGA TTA CTA CAG AAA ATA TGC AGC TAT C-3' SEQ ID NO: 18) and HCG-ANTISENT (SEQ ID NO: 16). This PCR contained µl glycalA (alpha-FSH) RT-PCR product as the template, and the following additional reagents:

1. 10 µl 10×PCR Buffer (Thermophilic DNA Polymerase 10× Buffer, magnesium Free M190G, Promega Madison Wis., USA)
2. 10 µl 25 mmol MgCl$_2$
3. 5 µl dNTPs stock solution containing 10 µmol each of dATP, dTTP, dCTP, and dGTP.
4. 1 µl of 100 pmol/µl primer HCG-SENTCACC (SEQ ID NO: 18) stock dilution
5. 1 µl of 100 pmol/µl primer HCG-ANTISENT (SEQ ID NO: 16) stock dilution
6. 2 µl TAQ (5 U/µl) (Taq DNA Polymerase in Storage Buffer A, Cat No. Mi865, Promega Madison Wis., USA)
7. 65 µl H$_2$O.

Cycling parameters were as follows: initial denaturation for 2 min at 95° C.; 30 cycles of amplification with each cycle consisting of 30 sec at 94° C., followed by 1 min at 50° C., and then 2 min at 68° C.; and a final extension for 10 min at 72° C.

This PCR product, termed CACCglycalA (SEQ ID NO: 19), was then inserted into the pLenti6/V5 D-TOPO vector according to manufacturer's instructions. This expression construct was named pLenti6/V5-glycalA.

This construct can be used for transient expression of the alpha-FSH subunit in in vitro cell culture. Alternatively, where stable expression of the alpha-FSH is desired, the pLenti6/V5-glycalA is transfected into the ViraPower 293FT-Producer cell line, along with the ViralPower packaging mix, to generate a packaged lentivirus (according to manufacturer's instructions: pLenti6/V5 Directional TOPO cloning kit, Invitrogen K4955-10). This packaged retrovirus is used to transduce a mammalian cell line in culture, producing a mammalian cell line that stably expresses the alpha-FSH subunit.

C. Creation of a Nucleic Acid Sequence Encoding Alpha-FSH+Beta-FSH (AB-FSH)

The alpha-FSH and beta-FSH encoding sequences described above were used to create a chimeric nucleic acid molecule alpha-beta FSH, in which the sequences encoding the mature beta-FSH protein (i.e., no signal peptide) were fused to the 3' end of sequences encoding the proprotein of alpha-FSH (i.e., including the signal peptide). The nucleotide sequence of alpha-beta-FSH (AB-FSH; SEQ ID NO: 20) was created using the PCR-based method described above for the production of X1X2 beta human FSH. This nucleotide sequence encodes the AB-FSH polypeptide (SEQ ID NO: 27).

1. Mature Beta-FSH

A PCR reaction was performed to generate a nucleic acid sequence encoding mature beta-FSH (i.e., lacking the signal peptide encoding sequences). This PCR reaction was performed using the new forward primer PFMX2 (5'-AAT AGC TGT GAG CTG ACC AA-3'; SEQ ID NO: 21) and the reverse primer PRX2 (SEQ ID NO: 10) on 1 µl of the purified X1X2 PCR product (see Example 1, above) solution as the template. This reaction contained additional reagents and was performed using the cycling parameters as described in Example 1A1 (*Isolation and amplification of two DNA segments each encoding one of two exons of beta-FSH*) above. The resulting PCR product was named S-FSH-B (SEQ ID NO: 22), and confirmed by 2% agarose gel electrophoresis (performed as described above; see FIG. 5, lane 2)

2. Proprotein Alpha-FSH

A second PCR reaction was performed to generate a nucleic acid sequence encoding the proprotein of alpha-FSH in which the stop codon was removed. Removal of the alpha-FSH stop codon is necessary to prevent premature truncation of the alpha-beta-FSH fusion protein. This PCR reaction was performed using the primer HCG-SENT (SEQ ID NO: 15) and the new primer HCG-ANTISENT/woTAA (5'-AGA TTT GTG ATA ATA ACA AGT ACT GCA GTG G-3'; SEQ ID NO: 23) on the glycalA PCR product (SEQ ID NO: 17) as template. This PCR contained 1 µl glycalA (alpha-FSH) PCR product as the template, and the following additional reagents:

1. 10 µl 10×PCR Buffer (Thermophilic DNA Polymerase 10× Buffer, magnesium Free M190G, Promega Madison Wis., USA)
2. 10 µl 25 mmol MgCl$_2$
3. 5 µl dNTPs stock solution containing 10 µmol each of dATP, dTTP, dCTP, and dGTP.
4. 1 µl of 100 pmol/µl primer HCG-SENT (SEQ ID NO: 15) stock dilution
5. 1 µl of 100 pmol/µl primer HCG-ANTISENT/woTAA (SEQ ID NO: 23) stock dilution
6. 2 µl TAQ (5 U/µl) (Taq DNA Polymerase in Storage Buffer A, Cat No. Mi865, Promega Madison Wis., USA)
7. 65 µl H$_2$O.

Cycling parameters were as follows: initial denaturation for 2 min at 95° C.; 30 cycles of amplification with each cycle consisting of 30 sec at 94° C., followed by 1 min at 50° C., and then 2 min at 68° C.; and a final extension for 10 min at 72° C. The resulting PCR product was named glycalwoTAA (SEQ ID NO: 24; alpha-FSH sequences without the TAA stop codon).

3. Alpha-Beta-FSH (AB-FSH)

A first PCR was performed to generate an intermediate nucleic acid molecule in which a short segment of 5' mature beta-FSH encoding sequence (S-FSH-B) was linked to the 3' end of the alpha-FSH sequence with the stop codon removed (glycalwoTAA). This PCR was performed using the glycalwoTAA PCR product as template, the forward primer HCG-SENT (SEQ ID NO: 15), and the hybrid reverse primer ABLIGATION (5'-<u>TTGGTCAGCTCACAGCTATTA</u> GAT TTG TGA TAA TAA CAA GTA CTG CAG TGG-3'; SEQ ID NO: 25), where the underlined sequence is the reverse complement of primer PFMX2 (SEQ ID NO: 21) and the sequence of primer ANTISENT/woTAA (SEQ ID NO: 23) is in italics. This PCR contained 1 µl glycalwoTAA PCR product as the template, and the following additional reagents:

1. 10 µl 10×PCR Buffer (Thermophilic DNA Polymerase 10× Buffer, magnesium Free M190G, Promega Madison Wis., USA)
2. 10 µl 25 mmol MgCl$_2$
3. 5 µl dNTPs stock solution containing 10 µmol each of dATP, dTTP, dCTP, and dGTP.
4. 1 µl of 100 pmol/µl primer HCG-SENT (SEQ ID NO: 15) stock dilution
5. 1 µl of 100 pmol/µl primer ABLIGATION (SEQ ID NO: 25) stock dilution
6. 2 µl TAQ (5 U/µl) (Taq DNA Polymerase in Storage Buffer A, Cat No. Mi865, Promega Madison Wis., USA)
7. 65 µl H$_2$O.

Cycling parameters were as follows: initial denaturation for 2 min at 95° C.; 30 cycles of amplification with each cycle consisting of 30 sec at 94° C., followed by 1 min at 50° C., and then 2 min at 68° C.; and a final extension for 10 min at 72° C. We named the product of this PCR Reaction glycalwoTAAUR (SEQ ID NO: 26).

A second PCR reaction was then performed to generate the final alpha-beta-FSH sequence (AB-FSH) using the glycalwoTAAUR intermediate PCR product (SEQ ID NO: 26) and the S-FSH-B PCR product (SEQ ID NO: 22) as templates. The PCR was performed using the forward primer HCG-SENT (SEQ ID NO: 15) and the reverse primer PRX2 (SEQ ID NO: 10). This PCR reaction contained the following reagents:

1. 10 µl 10×PCR Buffer (Thermophilic DNA Polymerase 10× Buffer, magnesium Free M190G, Promega Madison Wis., USA)
2. 10 µl 25 mmol $MgCl_2$
3. 5 µl dNTPs stock solution containing 10 µmol each of dATP, dTTP, dCTP, and dGTP.
4. 1 µl glycalwoTAAUR intermediate PCR product (SEQ ID NO: 26)
5. 1 µl X2 S-FSH-B PCR product (SEQ ID NO: 22)
6. 1 µl of 100 pmol/µl primer HCG-SENT (SEQ ID NO: 15) stock dilution
7. 1 µl of 100 pmol/µl primer PRX2 (SEQ ID NO: 10) stock dilution
8. 2 µl TAQ (5 U/µl) (Taq DNA Polymerase in Storage Buffer A, Cat No. Mi865, Promega Madison Wis., USA)
9. 65 µl $H_2O$ Cycling parameters were as follows: initial denaturation for 2 min at 95° C.; 30 cycles of amplification with each cycle consisting of 30 sec at 94° C., followed by 1 min at 50° C., and then 2 min at 68° C.; and a final extension for 10 min at 72° C. Cycling was performed using a PTC-100™ programmable Thermal Controller (MJ Research Inc, Watertown, Mass., USA).

The product of this PCR was confirmed to be AB-FSH (SEQ ID NO: 20) by 2% agarose gel electrophoresis (performed as described above; see FIG. 5, lane 4) and by sequencing of the pLenti/AB-FSH construct (see below) using vector primers.

The AB-FSH PCR product was then cloned into the pLenti6/V5 D-TOPO vector using the pLenti6/V5 Directional TOPO cloning kit according to manufacturer's instructions (Invitrogen K4955-10) as described above (Example 3B. "Alpha-FSH subunit encoding nucleic acid sequence") except that the PCR primers used to add the nucleotide sequence CACC were HCG-SENTCACC (SEQ ID NO: 18) and PRX2 (SEQ ID NO: 10). This expression construct was named pLenti/AB-FSH.

Example 4

Co-expression of Alpha-FSH and Beta-FSH in Mammalian Cell Culture

The pLenti6/V5-glycaLA (pLenti6/V5-D-topo vector containing the glycalA alpha-FSH insert) and the pTPKBFSH (pTargeT containing the SDK-X1X2 beta-FSH insert) expression constructs were used for the expression of the complete human FSH hormone in COS-7L (Invitrogen, catalog No. 11622016), and CHO-S (Invitrogen, catalog No. 11619012) cell lines. The alpha-FSH and beta-FSH expression constructs were co-transfected into the various cell lines using the LIPOFECTAMINE 2000 (Invitrogen) transfection reagent according to manufacturer's instructions. The expression vector pSV-β-Galactosidase (Promega) was included as a transfection control.

Following transfection, the cells were cultured in a selective medium containing 1000 µg/ml Geneticine and 400 µg/ml Blasticidin for 7 days. Geneticine-Blasticidine-resistant cells were transferred in a new culture medium containing Geneticine (200 µg/ml) and Blasticidin (200 µg/mL), and cultured to a cell density of $10^6$ cells/ml. The supernatant of this culture was than tested for the presence of the multisubunit (alpha subunit and beta subunit non-covalently associated) FSH complex.

The presence of the alpha and beta FSH complex was detected using the BIOSOURCE FSH-IRMA Kit (Biosource Europe S.A., Cat # KIP0841-KIP0844), an immunoradiometric assay kit for the quantitation of Follicle Stimulating Hormone (FSH). This FSH-IRMA assay is based on the use of two monoclonal antibodies, one specific for the alpha subunit of FSH and one for the beta subunit of FSH. Thus this assay only detects the complete alpha and beta FSH complex. The supernatant of pLenti6/V5-glycalA and the pTPKBFSH co-transfected cells was tested using the FSH-IRMA kit according to manufacturer's instructions. This assay indicated that the supernatant contains alpha and beta FSH complex in an amount of 110 U/ml.

Example 5

Expression of the Alpha-beta-FSH Fusion Protein in Mammalian Cell Culture

The alpha-beta-FSH expression construct pLenti/AB-FSH was transfected into COS-7L cells (Invitrogen, catalog No. 11622016) using the LIPOFECTAMINE 2000 (Invitrogen) transfection reagent according to manufacturer's instructions. The expression vector pSV-β-Galactosidase (Promega) was included as a transfection control.

Following transfection, the cells were cultured in a selective medium containing 400 µg/ml blasticidin (Gibco) for 7 days. Blasticidin-resistant cells were transferred in a new culture medium containing Geneticine at 200 µg/ml, and cultured to a cell density of $10^6$ cells/ml. These cells were then harvested and lysed. Cells were lysed by freezing and thawing in 1 mL of culture medium. The lysed cells were then centrifuged to pellet the cellular debris. The supernatant was then harvested and tested for the presence of alpha-beta-FSH.

The presence of the alpha-beta-FSH fusion protein was then detected using the BIOSOURCE FSH-IRMA Kit (Biosource Europe S.A., Cat # KIP0841-KIP0844), an immunoradiometric assay kit for the quantitation of Follicle Stimulating Hormone (FSH). This FSH-IRMA assay is based on the use of two monoclonal antibodies, one specific for the alfa subunit of FSH and one for the beta subunit of FSH. The supernatant of lysed pLenti/AB-FSH-transfected COS-7L cells was tested using the FSH-IRMA kit according to manufacturer's instructions. This assay indicated that the the chimeric alpha-beta-FSH protein was present at a concentration of 325 U/ml. Note that for this assay, this results indicates the amount of protein alpha-beta-FSH protein present, but this assay is not truly a functional assay.

To verify that the produced alpha-beta-FSH protein is biologically active, the supernatant of lysed pLenti/AB-FSH-transfected COS-7L cells is tested in the Granulosa assay as described in Example 2, supra. For this assay, 400 µl of GAB assay medium and 60 µL of granulosa cell suspension (~50,000-80,000 viable cells) are added to each well of a 24-well plate. Next, 40 µL of supernatant of lysed pLenti/AB-FSH-transfected COS-7L cells or of various concentrations of positive control recombinant FSH (Organon) are added to each well. The plates are then cultured for 3 days at 37° C. in a humidified 5% $CO_2$ incubator. The supernatant from each well is then harvested, and 10-20 µl of the supernatant assayed for estrogen levels by radioimunnoassay. Estrogen radioimmunoassay is performed using the Spectria RIA kit for estradiol measurement (Orion Diagnostic, Finland), according to the manufacturer's instructions.

For this assay, various concentrations of the positive control recombinant FSH (Organon) are tested and used to calculate a titration curve for FSH activity (recombinant FSH concentration in milliUnits per milliliter, mU/ml, versus estrogen radioimmunoassay values). This control curve is then used to interpolate the amount of biologically active alpha-beta-FSH. The alpha-beta-FSH of the invention shows a substantially higher activity profile in this assay, as expressed in Units of biligical activity per mg of protein, than the currently available recombinant FSH (Organon).

Example 6

Assembly of INF-β/INF-α2B Expression Constructs

The sequence of the genomic DNA encoding the INF-β is at Genbank Accession NM 002167. The cDNA sequence of the INF-β is SEQ ID NO: 28 (hereinafter referred to as THIMIOS1) and it corresponds to the above sequence NM 002167 without the stop codon. The sequence of the mature INF-α2B is a part of Genbank Accession Genbank NM 000605 (hereinafter referred to as PENNY1).

A PCR Amplification of Beta-FSH Encoding Sequences

1. Isolation and Amplification of Two DNA Segments Each Encoding One of Two Interferons (INF-β and INF-α2B)

Human genomic DNA was extracted from 50 μl of total blood using the Nucleo Spin Blood Quick Pure kit (Macherey-Nagel GmBH& Co.). The isolated DNA was then dissolved in 100 μl of TB Buffer (DNA solution). 10 μl of this DNA solution was used as template for two independent PCR reactions (5 μl genomic DNA solution per PCR reaction). The first PCR reaction was performed using primers specific for INF-β.

The forward primer has sequence ATGACCAACAAGT-GTCTCCTCCAAATTGCT (hereinafter referred to as THIMIOSF). The reverse primer without stopcodon has sequence GTTTCGGAGGTAACCTGTAAGTCTGTTAAT (hereinafter referred to as THIMIOSR). This PCR reaction amplifies the product CDS of INF-β.

The second PCR reaction was performed using primers specific for the mature chain of INF-α2B. The forward primer GACGACGACGACAAGTGTGATCTGCCTCAAACCCA (hereinafter referred to as PENNYF) contains 1-5 prime sequencing expressing an enterokinase site; this site has been added to give the expressed protein molecule the option to be cut, after production, thus providing, in case, two different products.

The mature INF-α2B sequence containing the enterokinase site (hereinafter referred to as PENNYF) corresponds to SEQ ID NO: 29.

The reverse primer is TCATTCCTTACTTCTTAAAC (hereinafter referred to as PENNYR).

Each independent PCR reaction contained 5 μl human genomic DNA solution as the template, and the following additional reagents:

1. 10 μl 10×PCR Buffer (Thermophilic DNA Polymerase 10× Buffer, magnesium Free M190G, Promega Madison Wis., USA)
2. 10 μl 25 mmol MgCl$_2$
3. 5 μl dNTPs stock solution containing 10 μmol each of dATP, dTTP, dCTP, and dGTP.
4. 1 μl of 100 pmol/μl forward primer stock dilution
5. 1 μl of 100 pmol/μl reverse primer stock dilution
6. 2 μl TAQ (5 U/μl) (Taq DNA Polymerase in Storage Buffer A, Cat No. Mi865, Promega Madison Wis., USA)
7. 65 μl H$_2$O.

Cycling parameters were as follows: initial denaturation for 2 min at 95° C.; 30 cycles of amplification with each cycle consisting of 30 sec at 94° C., followed by 30 sec at 50° C., and then 1 min at 72° C.; and a final extension for 5 min at 72° C. Cycling was performed using a PTC-100™ programmable Thermal Controller (MJ Research Inc, Watertown, Mass., USA).

Amplification of the INF-β and INF-α2B products PCR was confirmed by agarose gel (2% in TAE buffer) electrophoresis for 30 min at 125 mA using the DNA Molecular Weight Marker øX/Hinc II MK13a (HT Biotechnology Ltd., Cambridge, UK) as control molecular weight markers. The results are shown in FIG. 4 (see Lanes 2 and 3). The products of the PCR reaction were then purified using the PCR Cleanup Kit (Nucleospin Extract. Cat No. 740590.50).

The thus-obtained INF-β/INF-α2B with enterokinase sitecorresponds to SEQ ID NO: 30 whereas that without enterokinase sitecorresponds to SEQ ID NO: 31.

In an alternate strategy the final PCR product was generated by a single three primer PCR using the INF-β and INF-α2B products as templates and, as PCR primers, THIMIOSF, PENNYR and the ligation primer TINALEME having the sequence reported here-below.

ATCACACTTGTCGTCGTCGTTTCGGAGGTAACCTGTAAGTCT 1. 10 μl 10×PCR Buffer (Thermophilic DNA Polymerase 10× Buffer, magnesium Free M190G, Promega Madison Wis., USA)
2. 10 μl 25 mmol MgCl$_2$
3. 5 μl dNTPs stock solution containing 10 μmol each of dATP, dTTP, dCTP, and dGTP.
4. 2 μl THIMIOS1 PCR product
5. 2 μl HESEMESA PCR product
6. 1 μl of 100 pmol/μl forward primer stock THIMIOSF
7. 1 μl of 100 pmol/μl reverse primer stock PENNYR
8. 1 μl of 100 pmol/μl hybrid primer TINALEME
9. 2 μl TAQ (5 U/μl) (Taq DNA Polymerase in Storage Buffer A, Cat No. Mi865, Promega Madison Wis., USA)
10. 65 μl H$_2$O Cycling parameters were as follows: initial denaturation for 2 min at 95° C.; 30 cycles of amplification with each cycle consisting of 30 sec at 94° C., followed by 1 min at 50° C., and then 2 min at 68° C.; and a final extension for 10 min at 72° C. Cycling was performed using a PTC-100™ programmable Thermal Controller (MJ Research Inc, Watertown, Mass., USA).

Amplification of the product by this PCR reaction was confirmed by agarose (2% in TAE buffer) electrophoresis performed as described above. The product of this PCR reaction was then purified using the PCR Clean-up Kit (Nucleospin Extract. Cat No. 740590.50) to yield pure DNA in a final volume of 50 μl. Purity and size of the DNA was confirmed by agarose (2% in TAE buffer) electrophoresis performed as described above. The size of the product was determined by agarose gel electrophoresis.

The present invention is not to be limited in scope by the specific embodiments described herein. Indeed, various modifications of the invention in addition to those described herein will become apparent to those skilled in the art from the foregoing description and the accompanying figures.

Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A polypeptide comprising the amino acid sequence set forth in SEQ ID NO: 27, wherein the alpha FSH and beta FSH subunits of the of the polypeptide do not comprise intervening polypeptide sequences.

2. A polypeptide comprising an alpha FSH chain and a beta FSH chain, wherein said polypeptide comprises the amino acid sequence set forth in SEQ ID NO: 27, wherein said amino acid sequence is encoded by a single fusion polynucleotide sequence encoding the alpha FSH chain having its 3' end directly fused to the 5' end of the beta FSH chain.

* * * * *